(12) United States Patent
Beckmann et al.

(10) Patent No.: US 8,008,318 B2
(45) Date of Patent: Aug. 30, 2011

(54) 39-DESMETHOXY DERIVATIVES OF RAPAMYCIN

(75) Inventors: Christoph Hendrik Beckmann, Nr Saffron Walden (GB); Steven James Moss, Nr Saffron Walden (GB); Rose Mary Sheridan, Nr Saffron Walden (GB); Mingqiang Zhang, Nr Saffron Walden (GB); Barrie Wilkinson, Nr Saffron Walden (GB)

(73) Assignee: Biotica Technology Limited, Essex (GB)

( * ) Notice: Subject to any disclaimer, the term of this patent is extended or adjusted under 35 U.S.C. 154(b) by 0 days.

(21) Appl. No.: 12/630,251

(22) Filed: Dec. 3, 2009

(65) Prior Publication Data

US 2010/0081682 A1  Apr. 1, 2010

Related U.S. Application Data

(63) Continuation of application No. 11/908,250, filed as application No. PCT/GB2006/000853 on Mar. 10, 2006, now Pat. No. 7,648,996.

(30) Foreign Application Priority Data

Mar. 11, 2005 (GB) .................................. 0504994.5

(51) Int. Cl.
*A61P 35/00* (2006.01)
(52) U.S. Cl. ...................................................... 514/291
(58) Field of Classification Search ................... 514/291
See application file for complete search history.

(56) References Cited

U.S. PATENT DOCUMENTS

| | | |
|---|---|---|
| 3,929,992 A | 12/1975 | Sehgal et al. |
| 3,993,749 A | 11/1976 | Sehgal et al. |
| 4,439,196 A | 3/1984 | Higuchi |
| 4,447,224 A | 5/1984 | DeCant, Jr. et al. |
| 4,447,233 A | 5/1984 | Mayfield |
| 4,486,194 A | 12/1984 | Ferrara |
| 4,487,603 A | 12/1984 | Harris |
| 4,596,556 A | 6/1986 | Morrow et al. |
| 4,790,824 A | 12/1988 | Morrow et al. |
| 4,941,880 A | 7/1990 | Burns |
| 5,023,262 A | 6/1991 | Caufield et al. |
| 5,064,413 A | 11/1991 | McKinnon et al. |
| 5,138,051 A | 8/1992 | Hughes et al. |
| 5,206,018 A | 4/1993 | Sehgal et al. |
| 5,221,670 A | 6/1993 | Caufield |
| 5,312,335 A | 5/1994 | McKinnon et al. |
| 5,362,718 A | 11/1994 | Skotnicki et al. |
| 5,378,836 A | 1/1995 | Kao et al. |
| 5,383,851 A | 1/1995 | McKinnon, Jr. et al. |
| 5,391,730 A | 2/1995 | Skotnicki et al. |
| 5,399,163 A | 3/1995 | Peterson et al. |
| 5,432,183 A | 7/1995 | Schulte |
| 5,446,048 A | 8/1995 | Failli et al. |
| 5,563,145 A | 10/1996 | Failli et al. |
| 5,665,772 A | 9/1997 | Cottens et al. |
| 5,708,002 A | 1/1998 | Luly et al. |
| 5,712,129 A | 1/1998 | Ford |
| 5,728,710 A | 3/1998 | Luengo |
| 5,912,253 A | 6/1999 | Cottens et al. |
| 5,955,457 A | 9/1999 | Lee et al. |
| 6,015,815 A | 1/2000 | Mollison |
| 6,485,514 B1 | 11/2002 | Wrenn, Jr. |
| 7,183,289 B2 | 2/2007 | Zhang et al. |
| 2003/0176915 A1 | 9/2003 | Wright et al. |
| 2004/0147541 A1 | 7/2004 | Lane et al. |
| 2005/0032825 A1 | 2/2005 | Metcalf, III et al. |

FOREIGN PATENT DOCUMENTS

| | | |
|---|---|---|
| EP | 0663916 | 7/1995 |
| WO | 93/16189 | 8/1993 |
| WO | 9409010 | 4/1994 |
| WO | 9641807 | 12/1996 |
| WO | 98/02441 | 1/1998 |
| WO | 9804279 | 2/1998 |
| WO | 0103692 | 1/2001 |
| WO | 0181355 | 11/2001 |
| WO | 0187263 | 11/2001 |
| WO | 2004/007709 | 1/2004 |
| WO | 2004007709 | 1/2004 |
| WO | 2004101583 | 11/2004 |
| WO | 2006/016167 | 2/2006 |
| WO | 2006/095173 | 9/2006 |

OTHER PUBLICATIONS

Paiva, N. L., et al. "Incorporation of Acetate, Propionate, and Methionine Into Rapamcyin by Streptomyces Hygroscopicus." Journal of Natural Products, 54(1): 167-177 (Jan.-Feb. 1991).
Paiva, N. L., et al. "The immediate precursor of the nitrogen-containing ring of rapamycin in free pipecolic acid." Enzyme Microb, Technol. 15: 581-585 (Jul. 1993).
Perin, E. C. "Choosing a Drug-Eluting Stent A Comparison Between CYPHER and TAXUS." Reviews in Cardiovascular Medicine, 6 (suppl 1): S13-521 (2005).
Persidis, A. "Cancer multidrug resistance." Nature Biotechnology, 17: 94-95 (Jan. 1999).
Powell, N., et al. "The immunomodulatory drugs cyclosporin A, mycophenolate mofetil, and sirolimus (rapamycin) inhibit allergen-induced proliferation and IL-5 production by PBMCs from atopic asthmatic patients." Allergy Clin. Immunol., 108(6): 915-917 (2001).
Rabinovitch, A., et al. "Combination Therapy With Sirolimus and Interleukin-2 Prevents Spontaneous and Recurrent Autoimmune Diabetes in NOD Mice." Diabetes, 51: 638-345 (Mar. 2002).
Raught, B., et al. "The target of rapamycin (TOR) proteins." Proc. Natl. Acad. Sci. USA, 98(13): 7037-7044 (Jun. 19, 2001).
Reather, J. A. "Late steps in the biosynthesis of macrocyclic lactones." Ph.D. Dissertation, University of Cambridge (Apr. 2000).

(Continued)

*Primary Examiner* — Bruck Kifle
(74) *Attorney, Agent, or Firm* — Dann Dorfman Herrell & Skillman; Robert C. Netter, Jr.

(57) ABSTRACT

The present invention relates to 39-desmethoxyrapamycin derivatives and their uses thereof. The present invention provides for the use of these compounds in the treatment of cancer and/or B-cell malignancies, the induction or maintenance of immunosuppression, the treatment of transplantation rejection, graft vs. host disease, autoimmune disorders, diseases of inflammation, vascular disease and fibrotic diseases, the stimulation of neuronal regeneration or the treatment of fungal infections.

1 Claim, 6 Drawing Sheets

OTHER PUBLICATIONS

Reitamo, S., et al. "Efficacy of sirolimus (rapamycin) administered concomitantly with a subtherapeutic dose of cyclosporin in the treatment of severe psoriasis: a randomized controlled trial." British Journal of Dermatology, 145: 438-445 (2001).
Roth, T., et al. "Human Tumor Cell Lines Demonstrating the Characteristics of Patient Tumors as useful Models for Anticancer Drug Screening." In Feibig, H. H., et al. (ads), Relevance of Tumor Models for Anticancer Drug Development. Contrib. Oncol., 54: 145-156 (1999).
Roymans, D., et al. "Phosphatidylinositol 3-kinases in tumor progression," European Journal of Biochemistry, 268: 487-498 (2001).
Schwecke, T., et al. "The biosynthetic gene duster for the polyketide immunosuppressant rapamycin." Proc. Natl. Acad. Sci. USA, 92: 7839-71343 (Aug. 1995).
Sedrani, R., et al. "Chemical Modification of Rapamycin: The Discovery of SDZ RAD." Transplantation Proceedings, 30: 2192-2194 (1998).
Sehgal, R., et al. "Rapamycin (AY-22,989), A New Antifungal Antibiotic: II. Fermentation, Isolation and Characterization." Journal of Antibiotics, 38(10): 1975).
Shepherd, P. R., et al. "Phosphoinositide 3-kinase: the key switch mechanism in insulin signalling." Biochemical Journal, 33: 471-490 (1999).
Steiner, U., et al. "Expression of Multidrug Resistance Genes MVP, MDR1, and MRP1 Determined Sequentially Before, During, and After Hyperthermic Isolated Limb Perfusion of Soft Tissue Sarcoma and Melanoma Patients." Journal of Clinical Oncology, 20(15): 3282-3292 (Aug. 1, 2002).
Stein, J. P., et al. "Neurotrophic immunophilin ligands stimulate structural and functional recovery in neurodegenerative animal models." Proc. Natl. Acad. Sal. USA, 94: 2019-2024 (Mar. 1997).
Szakacs, G., et al. "Predicting drug sensitivity and resistance: Profiling ABC transporter genes in cancer cells." Cancer Cell, 6: 129-137 (Aug. 2004).
Tanford, C. "Protein Denaturation." Adv. Prot. Chem., 23: 121-282 (1968).
Tanford, C. "Protein Denaturation: Part C. Theoretical Models for the mechanism of denaturation." Adv. Prot Chem., 24: 1-95 (1970).
Tang, S. J., et al. "A rapamycin-sensitive signaling pathway contributes to long-term synaptic plasticity in the hippocampus." Proc. Natl. Acad. Sci. USA, 99(1): 467-472 (Jan. 8, 2002).
Tee, A. R., et al. "Caspase Cleavage of Initiation Factor 4E-Binding Protein 1 Yields a Dominant Inhibitor of Cap-Dependent Translation and Reveals a Novel Regulatory Motif." Molecular and Cellular Biology, 22(6): 1674-1683 (Mar. 2002).
Toshima, K., et al. "Recent Progress in O-Glycosylation Methods and Its Application to Natural Products Synthesis." Chemical Review, 93: 1503-1531 (1983).
Trepanier, D. J. et al. "Rapamycln: Distribution, Pharmacokinetics and Therapeutic Range Investigations: An Update." Clinical Biochemistry, 31(5): 345-351 (1998).
Vezina, C. at al. "Rapamycin (AY-22,989), A New Antifungal Antibiotic: I. Taxonomy of the Producing Streptomycete and Isolation of the Active Principle." Journal of Antibiotics, 28: 721-728 (1975).
Volpe, D. et al. "Towards Standardization of an In Vitro Method of Drug Absorption." Pharmacopeial Forum, 27(4): 2916-2922 (Jul.-Aug. 2001).
Waller, J. R., et al. "Molecular mechanism and renal allograft fibrosis." British Journal of Surgery, 88: 1429-1441 (2001).
Warner, L. M., et al. "A Modification of the in Vivo Mixed Lymphocyte Reaction and Rapamycin's Effect in This Model." Clinical Immunology and Immunopathology, 34(3): 242-247 (Sep. 1992).
Yu, K., et al. "mTOR, a novel target in breast cancer: the effect of CCI-779, an mTOR inhibitor, in preclinical models of breast cancer." Endocrine-Related Cancer, 8: 249-258 (2001).
Zhu, J., et al. "Rapamycin Inhibits Hepatic Stellate Cell Proliferation in Vitro and Limits Fibrogenesis in an In Vivo Model of Liver Fibrosis." Gastroenterology: 117: 1198-1204 (1999).
March, J. March's Advanced Organic Chemistry, 4th Ed, John Wiley & Sons, U.K. (2001).

Alarcon, C. M., et al. "Protein Kinase Activity and Identification of a Toxic Effector Domain of the Target of Rapamycin TOR Proteins in Yeast." Molecular Biology of the Cell, 10(8): 2531-2546 (Aug. 1999).
Alvarez, M., et al. "Generation of a Drug Resistance Profile by Quantification of mdr-1/P-Glycoprotein in the Cell Lines of the National Cancer Institute Anticancer Drug Screen." Journal of Clinical Investigation, 95: 2205-2214 (May 1995).
Aparicio, J. F., et al. "Organization of the biosynthetic gene cluster for rapamycin in Streptomyces hygroscopicus: analysis of the enzymatic domains in the modular polyketide synthase," Gene, 169: 9-16 (1996).
Baker, H., et al. "Rapamycin (AY-22,989), A New Antifungal Antibiotic: III. In Vitro and In Vivo Evaluation." Journal of Antibiotics, 31(6): 539-545 (1978).
Boulay, A., et al. "Antitumor Efficacy of Intermittent Treatment Schedules with the Rapamycin Derivative RAD001 Correlates with Prolonged Inactivation of Ribosomal Protein S6 Kinase 1 in Peripheral Blood Mononuclear Cells." Cancer Research, 64: 252-261 (Jan. 1, 2004).
Boyd, M. R., et al. "Some Practical Considerations and Application of the National Cancer Institute In Vitro Anticancer Drug Discovery Screen." Drug Development Research, 34: 91-109 (1995).
Brown, E. J., et al. "A mammalian protein targeted by G1-arresting rapamycin-receptor complex." Nature, 369: 756-758 (Jun. 30, 1994).
Brunn, G. J., et al. "Direct inhibition of the signaling functions of the mammalian target of rapamycin by the phosphoinositide 3-kinase inhibitors, wortmannin and LY294002." EMBO Journal, 15(19): 5256-5287 (1996).
Brunn, G. J. et al. "The Mammalian Target of Rapamycin Phosphorylates Sites Having a (Ser/Thr)-Pro Motif and Is Activated by Anitbodies to a Region near Its COOH Terminus." Journal of Biological Chemistry, 272(51): 32547-32550 (Dec. 19, 1997).
Carlson, R. P., et al. "Rapamycin, a Potential Disease-Modifying Antiarthritic Drug." Journal of Pharmacology and Experimental Therapeutics, 286(2): 1125-1138 (1993).
Crowe, A., et al. "Absorption and Intestinal Metabolism of SDZ-RAD and Rapamycin in Rats." Drug Metabolism and Disposition, 27(5): 627-632 (1999).
Dengler, W. A., et al. "Development of a propidium iodide fluorescence assay for proliferative and cytotoxicity assays." Anti-Cancer Drugs, 6: 522-532 (1995).
DiLella, A. G., et al. "Exon Organization of the Human FKBP-12 Gene: Correlation with Structural and Functional Protein Domains." Biochemistry, 30: 8512-8517 (1991).
Dudkin, L., et al. "Biochemical Correlates of mTOR Inhibition by the Rapamycin Ester CCI-779 and Tumor Growth Inhibition." Clinical Cancer Research, 7: 1758-1764 (Jun. 2001).
Evans, D. A., et al. "Asymmetric Synthesis of Calyculin A. 3. Assemblage of the Calyculin Skeleton and the Introduction of a New Phosphate Monoester Synthesis." Journal of Organic Chemistry, 57: 1964-1966(1992).
Fiebig, H. H., et al. "Human Tumor Xenografts: Predictivity, Characterization and Discovery of New Anticancer Agents." in Fiebig, H. H., et al (eds). Relevance of Tumor Models for Anticancer Drug Development. Contrib. Oncol., 54: 29-50 (1999).
Findlay, J. A., et ak. "On the chemistry and high field nuclear magnetic resonance spectroscopy of rapamycin." Canadian Journal of Chemistry, 58: 579 (1980).
Fishbein, T. M., et al. "Intestinal Transplantation Before and After the Introduction of Sirolimus." Transplantation, 73: 10: 1538-1542 (May 27, 2002).
Foey, A., et al. "Cytokine-stimulated T cells induce macrophage IL010 production dependent on phosphatidylinositol 3-kinase and p70S6K Implication for rheumatoid arthritis." Arthritis Research, 4(1): 64-70 (Oct. 10, 2001).
Furniss, B. S., et al. Vogel's textbook of practical organic chemistry, 5th ed. Pearson, Prentice Hall, Harlow, UK, (1989).
Gallant-Haidner, H. L., et al. "Pharmacokinetics and Metabolism of Sirolimus." Therapeutic Drug Monitoring, 22 (1): 31-35 (2000).
Grass, G. M., et al. "Evaluation of CACO-2 monolayers as a predictor of drug permeability in colonic tissues." FASEB Journal, 6: A1002 (1992).

Greene, T. W., et al. Protective Groups in Organic Synthesis, 2nd Ed. J. Wiley & Sons (1991).

Gregory, C. R., et al. "Rapamycin Inhibits Arterial Intimal Thickening Caused by Both Alloimmune and Mechanical Injury." Transplantation: 55(6): 1409-1418 (2004).

Gregory, M. A., et al. "Isolation and Characterization of Pre-rapamycin, the First Macrocyclic Intermediate in the Biosynthesis of the Immunosuppressant Rapamycin by S. hygroscopicus." Angew Chem. Int. Ed. Engl., 43(19): 2551-2553 (2004).

Gu, J., et al. "Lipase-Catalyzed Regloselective Esterification of Rapamcyin: Synthesis of Temsirolimus (CCI-779)." Organic Letters, 7(18): 3945-3948 (2005).

Guba, M., et al. "Rapamycin inhibits primary and metastatic tumor growth by antiangiogenesis: involvement of vascular endothelial growth factor." Nature Medicine, 8(2): 128-135 (Feb. 2002).

Hardwick, J. S., et al. "Rapamycin-modulated transcription defines the subset of nutrient-sensitive signaling pathways directly controlled by the Tor proteins." Proc. Natl. Acad. Sci. USA, 96(26): 14866-14870 (Dec. 21, 1999).

Hentges, K E., et al. "FRAP/mTOR is required for proliferative and patterning during embryonic development in the mouse." Proc. Natl. Acad, Sci. USA, 98(24): 13798-13801 (Nov. 20, 2001).

Huang, S., et al. "Mechanisms of resistance to rapamycins." Drug Resistance Updates, 4: 378-391 (2001).

Jain, S., et al. "Rapamycin Reduces Expression of Fibrosis-Associated Genes in an Experimental Model of Renal Ischaemla Reperfuslon Inury." Transplantation Proceedings, 33: 556-558 (2001).

Kahan, B. D. et al. "Preclinical Evaluation of a New Potent Immunosuppressive Agent, Rapamycin." Transplantation, 52(2): 185-191 (Aug. 1991).

Kahan, B. D., et al. "Rapamycin: Clinical Results and Future Opportunities." Transplantation, 72(7): 1181-1193 (Oct. 15, 2001).

Kirby, B., et al. "Psoriasis: the future." British Journal of Dermatology, 144: 37-43 (2001).

Kirchner, G., I., et al. "Pharmacokinetics of SDZ RAD and cyclosporin including their metabolites in seven kidney graft patients after the first dose of SDZ RAD," Journal of Clinical Pharmacology, 50: 449-454 (2000).

Kuo, C. J., et al "Rapamycin selectively inhibits interleukin-2 activation of p70 S6 kinase." Nature, 358: 70-73 (Jul. 2, 1992).

Langman, T., et al. "Real-Time Reverse Transcription-PCR Expression Profiling of the Complete Human ATP-Binding Binding Cassette Transporter Superfamily in Various Tissues." Clinical Chemistry, 49(2): 230-238 (2003).

Lee, J., et al, "Rhodamine Efflux Patterns Predict P-glycoprotein Substrates in the National Cancer Institute Drug Screen." Molecular Pharmacology, 46: 627-638 (1994).

Li, A. P. "Screening for human ADME/Tox drug properties in drug discovery." Drug Discovery Today, 6(7): 357-36 (Apr. 2001).

Lowden, P. A. S. "Studies on the Biosynthesis of Rapamycin." Ph.D. Dissertation, University of Cambridge (Mar. 1997).

Lyons, W. E., et al. "Immunosuppressant FK506 promotes neurite outgrowth in cultures of PC12 cells and sensory ganglia." Proc. Natl. Acad. Sci. USA, 91: 3191-3195 (Apr. 1994).

Main, E. R. G., et al. "Context-Dependent Nature of Destabilizing Mutations on the Stability of FKBP." Biochemistry, 37: 6145-3153 (1998).

Main, E. R. G. et al. "Folding Pathway of FKBP12 and Characterisation of the Transition State." Journal of Molecular Biology, 291: 429-444 (1999).

McAlpine, J. B., et al. "Revised NMR Assignments for Rapamycin." Journal of Antibiotics, 44: 688-690 (Jun. 1991).

Meiering, E. M., et al. "Effect of Active Site Residues in Barnase on Activity and Stability." Journal of Molecular Biology, 225: 585-580 (1992).

Morice, M., et al. "A Randomized Comparison of a Sirolimus-Eluting Stent With a Standard Stent for Coronary Revascularization." New England Journal of Medicine, 346(23): 1773-1780 (Jun. 6, 2002).

Mothe-Satney, I., et al. "Mammalian Target of Rapamycin-dependent Phosphorylation of PHAS-I in Four (S/T)P Sites Detected by Phospho-specific Antibodies." Journal of Biological Chemistry, 275(43): 33836-33843 (Oct. 27, 2000).

Myckatyn, T. M., et al. "The Effects of Rapamycin in Murine Peripheral Nerve Isografts and Allografts." Plastic and Reconstructive Surgery, 109(7): 2405-2417 (2002).

Nave, B. T., et al. "Mammalian target of rapamycin is a direct target for protein kinase B: identification of a convergence point for opposing effects of insulin and amino-acid deficiency on protein translation." Biochemical Journal, 344: 427-431 (1999).

NCCLS Reference Method for Broth Dilution Antifungal Susceptibility Testing for Yeasts: Approved Standard M27-A2, 22(15), ( 2002).

Gregory, M.A., et al., "Mutasynthesis of rapamycin analogues through the manipulation of a gene governing starter unit biosynthesis," Angewandte Chemie (International Ed. In English), 44(30):4757-4760, (Jul. 25, 2005).

Lowden, P.A.S., et al., "New rapamycln derivatives by precursor-directed biosynthesis," Chembiochem: A European Journal of Chemical Biology, 5(4):535-538, (Apr. 2, 2004).

Gregory, M.A., et al., "566 novel mT0R inhibitors with improved pharmacological properties over rapamycin," European Journal of Cancer, Supplement, 2(8):172, (Sep. 2004). [Abstract].

Hamilton, G.S., et al., "Neuroimmunophilin ligands as novel therapeutics for the treatment of degenerative disorders of the nervous system," Current Pharmaceutical Design, 3(4):405-428, (1997). [Abstract].

Cecil, Textbook of Medicine, 21st Edition (2000), Goldman & Bennett (Editors), W.B. Saunders Company (Publisher), Chapter 198, pp. 1060-1074.

Dhooge C et al., "P-glycoprotein is an independent prognostic factor predicting relapse in childhood acute lymphoblastic leukaemia: results of a 60year prospective study," 1999 British J Haematol. 105: 676-683.

Bown V, et al., "Rapamycn is active against B-precursor leukemai in vitro and in vivo, an effect that is modulated by IL-7-mediated signaling," 2003 PNAS 100(25): 15113-15118.

Gajra A, "Lymphoma, B-Cell," eMedicine, Jan. 10, 2005, retrieved from the Internet on Nov. 20, 2005 from http://ermedicine.com/med/topic1358.htm.

Fu, L.W., et al., "The multidrug resistance of tumour cells was reversed by tetradrine in vitro and in xenografts derived from human brest adenocarcinoma MCF-7/adr cells," European Journal of Cancer, 28:418-426, (2002).

Trepanier, D.J., et al., "Rapamycin: Distribution, Pharmacokinetics and Therapeutic Range Investigations: An Update," Clinical Biochemistry, 31:345-351, (1998).

Gallant-Haidner, H.L., et al., "Pharmacokinetics and Metabolism of Sirolimus," Therapeutic Drug Monitoring, 22:31-35, (2000).

U.S. Appl. No. 11/908,367, filed Sep. 11, 2007; First named inventor: Rose Mary Sheridan.

A

B

39-DESMETHOXY DERIVATIVES OF RAPAMYCIN

CROSS-REFERENCE TO RELATED APPLICATIONS

This is a continuation of copending application(s) application Ser. No. 11/908,250 filed on Sep. 10, 2007, which is a 371 National Stage of PCT/GB2006/000853 filed Mar. 10, 2006, which claims the benefit of United Kingdom application number 0504994.5 filed on Mar. 11, 2005 the entire disclosure of which is hereby incorporated by reference.

FIELD OF THE INVENTION

The present invention relates to novel 39-desmethoxyrapamycin derivatives and uses thereof. In a further aspect the present invention provides for the use of these 39-desmethoxyrapamycin derivatives in the treatment of cancer and/or B-cell malignancies, the induction or maintenance of immunosuppression, the treatment of transplantation rejection, graft vs. host disease, autoimmune disorders, diseases of inflammation, vascular disease and fibrotic diseases, the stimulation of neuronal regeneration or the treatment of fungal infections.

BACKGROUND OF THE INVENTION

Rapamycin (sirolimus) (FIG. 1) is a lipophilic macrolide produced by *Streptomyces hygroscopicus* NRRL 5491 (Sehgal et al. 1975; Vézina et al., 1975; U.S. Pat. Nos. 3,929,992; 3,993,749) with a 1,2,3-tricarbonyl moiety linked to a pipecolic acid lactone (Paiva et al., 1991). For the purpose of this invention rapamycin is described by the numbering convention of McAlpine et al. (1991) in preference to the numbering conventions of Findlay et al. (1980) or Chemical Abstracts (11$^{th}$ Cumulative Index, 1982-1986 p60719CS).

Rapamycin has significant pharmacological value due to the wide spectrum of activities exhibited by the compound. Rapamycin shows moderate antifungal activity, mainly against *Candida* species but also against filamentous fungi (Baker et al., 1978; Sehgal et al., 1975; Vézina et al., 1975; U.S. Pat. Nos. 3,929,992; 3,993,749). Rapamycin inhibits cell proliferation by targeting signal transduction pathways in a variety of cell types, e.g. by inhibiting signalling pathways that allow progression from the $G_1$ to the S-phase of the cell cycle (Kuo et al., 1992). In T cells rapamycin inhibits signalling from the IL-2 receptor and subsequent autoproliferation of the T cells resulting in immunosuppression. The inhibitory effects of rapamycin are not limited to T cells, since rapamycin inhibits the proliferation of many mammalian cell types (Brunn et al., 1996). Rapamycin is, therefore, a potent immunosuppressant with established or predicted therapeutic applications in the prevention of organ allograft rejection and in the treatment of autoimmune diseases (Kahan et al., 1991). 40-O-(2-hydroxy)ethyl-rapamycin (SDZ RAD, RAD 001, Certican, everolimus) is a semi-synthetic analogue of rapamycin that shows immunosuppressive pharmacological effects and is also under investigation as an anticancer agent (Sedrani, R. et al., 1998; Kirchner et al., 2000; U.S. Pat. No. 5,665,772, Boulay et al, 2004). Approval for this drug as an immunosuppressant was obtained for Europe in 2003. The rapamycin ester derivative CCI-779 (Wyeth-Ayerst) inhibits cell growth in vitro and inhibits tumour growth in vivo (Yu et al., 2001). CCI-779 is currently in Phase III clinical trials as a potential anti-cancer agent. The value of rapamycin in the treatment of chronic plaque psoriasis (Kirby and Griffiths, 2001), the potential use of effects such as the stimulation of neurite outgrowth in PC12 cells (Lyons et al., 1994), the block of the proliferative responses to cytokines by vascular and smooth muscle cells after mechanical injury (Gregory et al., 1993) and its role in prevention of allograft fibrosis (Waller and Nicholson, 2001) are areas of intense research (Kahan and Camardo, 2001). Recent reports reveal that rapamycin is associated with a lower incidence of cancer in organ allograft patients on long-term immunosuppressive therapy than those on other immunosuppressive regimes, and that this reduced cancer incidence is due to inhibition of angiogenesis (Guba et al., 2002). It has been reported that the neurotrophic activities of immunophilin ligands are independent of their immunosuppressive activity (Steiner et al., 1997) and that nerve growth stimulation is promoted by disruption of the mature steroid receptor complex as outlined in the patent application WO 01/03692. Side effects such as hyperlipidemia and thrombocytopenia as well as potential teratogenic effects have been reported (Hentges et al., 2001; Kahan and Camardo, 2001).

The polyketide backbone of rapamycin is synthesised by head-to-tail condensation of a total of seven propionate and seven acetate units to a shikimate derived cyclohexanecarboxylic acid starter unit by the very large, multifunctional proteins that comprise the Type I polyketide synthase (rap PKS, Paiva et al., 1991). The L-lysine derived amino acid, pipecolic acid, is condensed via an amide linkage onto the last acetate of the polyketide backbone (Paiva et al., 1993) and is followed by lactonisation to form the macrocycle.

The nucleotide sequences for each of the three rapamycin PKS genes, the NRPS-encoding gene and the flanking late gene sequences and the corresponding polypeptides, were identified by Aparicio et al., 1996, and Schwecke et al., 1995 and were deposited with the NCBI under accession number X86780, and corrections to this sequence have recently been published in WO 04/007709.

The first enzyme-free product of the rapamycin biosynthetic cluster has been designated pre-rapamycin (WO 04/007709, Gregory et al., 2004). Production of the fully processed rapamycin requires additional processing of the polyketide/NRPS core by the enzymes encoded by the rapamycin late genes, RapJ, RapN, RapO, RapM, RapQ and RapI.

The pharmacologic actions of rapamycin characterised to date are believed to be mediated by the interaction with cytosolic receptors termed FKBPs. The major intracellular rapamycin receptor in eukaryotic T-cells is FKBP12 (DiLella and Craig, 1991) and the resulting complex interacts specifically with target proteins to inhibit the signal transduction cascade of the cell.

The target of the rapamycin-FKBP12 complex has been identified in yeast as TOR (target of rapamycin) (Alarcon et al., 1999) and the mammalian protein is known as FRAP (FKBP-rapamycin associated protein) or mTOR (mammalian target of rapamycin) (Brown et al. 1994).

A link between mTOR signalling and localized protein synthesis in neurons; its effect on the phosphorylation state of proteins involved in translational control; the abundance of components of the translation machinery at the transcriptional and translational levels; control of amino acid permease activity and the coordination of the transcription of many enzymes involved in metabolic pathways have been described (Raught et al., 2001). Rapamycin sensitive signalling pathways also appear to play an important role in embryonic brain development, learning and memory formation (Tang et al., 2002). Research on TOR proteins in yeast also revealed their roles in modulating nutrient-sensitive signalling pathways (Hardwick et al., 1999). Similarly, mTOR has been identified as a direct target for the action of protein kinase B (akt) and of having a key role in insulin signalling (Shepherd et al., 1998; Navé et al., 1999). Mammalian TOR has also been implicated in the polarization of the actin cytoskeleton and the regulation of translational initiation (Alarcon et al., 1999). Phosphatidylinositol 3-kinases, such as mTOR, are functional in several aspects of the pathogenesis of tumours such as cell-cycle progression, adhesion, cell survival and angiogenesis (Roymans and Slegers, 2001).

Pharmacokinetic studies of rapamycin and rapamycin analogues have demonstrated the need for the development of novel rapamycin compounds that may be more stable in solution, more resistant to metabolic attack and/or have improved cell membrane permeability and decreased efflux and which therefore may exhibit improved oral bio-availability.

A range of synthesised rapamycin analogues using the chemically available sites of the molecule has been reported. The description of the following compounds was adapted to the numbering system of the rapamycin molecule described in FIG. 1. Chemically available sites on the molecule for derivatisation or replacement include C40 and C28 hydroxyl groups (e.g. U.S. Pat. Nos. 5,665,772; 5,362,718), C39 and C16 methoxy groups (e.g. WO 96/41807; U.S. Pat. No. 5,728,710), C32, C26 and C9 keto groups (e.g. U.S. Pat. Nos. 5,378,836; 5,138,051; 5,665,772). Hydrogenation at C17, C19 and/or C21, targeting the triene, resulted in retention of antifungal activity but relative loss of immunosuppression (e.g. U.S. Pat. Nos. 5,391,730; 5,023,262). Significant improvements in the stability of the molecule (e.g. formation of oximes at C32, C40 and/or C28, U.S. Pat. Nos. 5,563,145, 5,446,048), resistance to metabolic attack (e.g. U.S. Pat. No. 5,912,253), bioavailability (e.g. U.S. Pat. Nos. 5,221,670; 5,955,457; WO 98/04279) and the production of prodrugs (e.g. U.S. Pat. Nos. 6,015,815; 5,432,183) have been achieved through derivatisation.

However, there remains a need for a greater range of rapamycin derivatives with improved metabolic stability, improved cell membrane permeability and/or a decreased rate of efflux. Such rapamycin derivatives would have great utility in the treatment of a wide range of conditions. The present invention provides a range of 39-desmethoxyrapamycin derivatives with improved metabolic stability, improved cell membrane permeability and/or a decreased rate of efflux and/or a different cell inhibitory profile to rapamycin. Such compounds are useful in medicine, in particular for the treatment of cancer and/or B-cell malignancies, the induction or maintenance of immunosuppression, the treatment of transplantation rejection, graft vs. host disease, autoimmune disorders, diseases of inflammation, vascular disease and fibrotic diseases, the stimulation of neuronal regeneration or the treatment of fungal infections.

SUMMARY OF THE INVENTION

The present invention provides 39-desmethoxy derivatives of rapamycin, methods for the preparation of these compounds, intermediates thereto and methods for the use of these compounds in medicine.

In its broadest aspect the present invention provides 39-desmethoxy derivatives of rapamycin characterised in that the 40-hydroxy position is derivatised as a carboxylic acid ester, as an ether, as a phosphate ester, as a phosphinate ester, as an acetal or as a glycosyl.

The metabolic stability, cell membrane permeability, efflux and bioavailability of the compounds of the invention may be tested as set out below.

When 39-desmethoxyrapamycin is derivatised as a carboxylic acid ester, as an ether or as an acetal the derivatising group preferably contains no more than 12 carbon atoms (especially 7 or fewer particularly 5 or fewer carbon atoms). Preferably it contains at least one functional group (especially at least two functional groups) selected from —CF$_2$PO(OH)$_2$, —PO(OH)$_2$, —COOH, —OH and —NH$_2$ particularly selected from —COOH and —OH more particularly —OH.

When 39-desmethoxyrapamycin is derivatised as an acetal derived from a glycosyl group preferably each glycosyl is formed from a sugar or a glycoside which preferably contains no more than 12 carbon atoms (especially 7 or fewer, particularly 6 or fewer carbon atoms). Examples include mono and disaccharides, particularly monosaccharides which form 5 and 6 membered rings. Preferably it contains at least one functional group (especially at least two function groups) selected from —COOH, —OH and —NH$_2$ particularly selected from —NH$_2$ and —OH more particularly —OH.

When 39-desmethoxyrapamycin is derivatised as a phosphate ester preferably the alkyl groups contain no more than 4 carbon atoms.

When 39-desmethoxyrapamycin is derivatised as a phosphinate ester preferably the alkyl groups preferably contain no more than 4 carbon atoms, an example is the ester formed with phosphinic acid.

Specific examples of derivatising moieties are given below.

In a more specific aspect the present invention provides 39-desmethoxyrapamycin derivatives according to formula (I) below, or a pharmaceutically acceptable salt thereof:

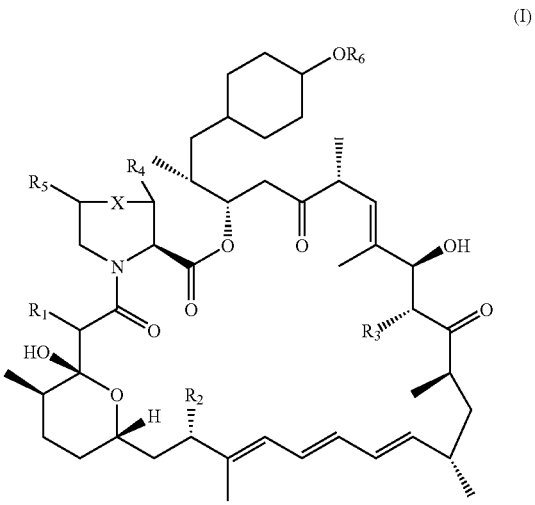

(I)

wherein:
X represents bond or CH$_2$;
R$_1$ represents a keto group or (H,H);
R$_2$ represents OH or OMe;
R$_3$ represents H, OH or OMe;
R$_4$ and R$_5$ each independently represent H or OH;
R$_6$ represents —R$_7$, —C(O)R$_7$, —(CH$_2$)$_2$—O—[CR$_{21}$R$_{22}$—O]$_a$—C(O)—R$_{23}$;  —CR$_{21}$R$_{22}$—O—C(O)—R$_{23}$; —POR$_{19}$R$_{20}$, —PO(OR$_{19}$)(OR$_{20}$) or Y—R$_{15}$;
R$_7$ represents —(CR$_8$R$_9$)$_m$(CR$_{10}$R$_{11}$)$_p$CR$_{12}$R$_{13}$R$_{14}$;
R$_8$ and R$_9$ each independently represent C1-C4 alkyl, C2-C4 alkenyl or C2-C4 alkynyl, any of which groups may optionally be substituted with —PO(OH)$_2$, —CF$_2$PO (OH)$_2$, —OH, —COOH or —NH$_2$; or R$_8$ and R$_9$ each independently represent H, trifluoromethyl or F;

R$_{10}$, R$_{11}$, R$_{12}$, R$_{13}$ and R$_{14}$ each independently represent C1-C4 alkyl, C2-C4 alkenyl or C2-C4 alkynyl, any of which groups may optionally be substituted with —PO(OH)$_2$, —CF$_2$PO(OH)$_2$, —OH, —COOH or —NH$_2$; or R$_{10}$, R$_{11}$, R$_{12}$, R$_{13}$ and R$_{14}$ may be independently selected from H, —(CR$_8$R$_9$)$_q$NH$_2$, —(CR$_8$R$_9$)$_q$OH, CF$_3$, F, COOH; or R$_{10}$ and R$_{11}$ or R$_{12}$ and R$_{13}$ or R$_{13}$ and R$_{14}$ may be taken together with the carbon to which they are joined to form a C3-C6 cycloalkyl or a 3 to 6 membered heteroalkyl ring that contains one or more heteroatoms selected from N, O and S and that is optionally, substituted with up to 5 —(CR$_8$R$_9$)$_q$OH, —(CR$_8$R$_9$)$_q$NH$_2$ or COOH groups; Y=bond, —C(O)—O—; —(CH$_2$)$_2$—O—C(O)—O—;

R$_{15}$ represents

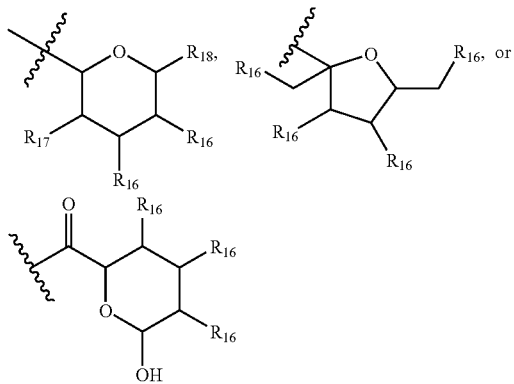

R$_{16}$ are each independently H or OH;
R$_{17}$ is independently selected from H, OH and NH$_2$;
R$_{18}$ is independently selected from H, —CH$_3$, —CH$_2$OH and —COOH;
provided however that no more than 2 groups selected from R$_{16}$, R$_{17}$ and R$_{16}$ represent H or CH$_3$;
R$_{19}$ and R$_{20}$ each independently represent H or C1-C4 alkyl or R$_{19}$ and R$_{20}$ together represent =CH$_2$;
R$_{21}$ is independently selected from H, CH$_3$;
R$_{22}$ is independently selected from H, —CH$_3$, —CH=CH$_2$, —CH$_2$Cl, —CHCl$_2$, —CCl$_3$, —CH(OH)Me, —CH$_2$OH, —CH$_2$CH$_3$, —CH(Cl)Me;
R$_{23}$ is independently R$_7$, Y—R$_{15}$ or a 5 or 6 membered aryl or heteroaryl ring optionally substituted with between one and three groups selected from OH, F, Cl, Br, NO$_2$ and NH$_2$;
a represents 0 or 1;
m, p and q each independently represent an integer between 0-4;
provided however that the R$_7$ moiety does not contain more than 12 carbon atoms and does contain at least one functional group selected from —PO(OH)$_2$, —CF$_2$PO(OH)$_2$, —COOH, OH or NH$_2$; or a pharmaceutically acceptable salt thereof.

The above structure shows a representative tautomer and the invention embraces all tautomers of the compounds of formula (I) for example keto compounds where enol compounds are illustrated and vice versa.

Unless particular stereoisomers are specifically indicated (e.g. by a bolded or dashed bond at a relevant stereocentre in a structural formula, by depiction of a double bond as having E or Z configuration in a structural formula, or by using stereochemistry-designating nomenclature), all stereoisomers are included within the scope of the invention as pure compounds as well as mixtures thereof. Unless otherwise indicated, individual enantiomers, diastereomers, geometrical isomers, and combinations and mixtures thereof are all encompassed by the present invention. Polymorphic crystalline forms and solvates and hydrates are also encompassed within the scope of this invention.

In a further aspect, the present invention provides 39-desmethoxyrapamycin derivatives such as compounds of formula (I) or a pharmaceutically acceptable salt thereof, for use as a pharmaceutical.

Definitions

The articles "a" and "an" are used herein to refer to one or to more than one (i.e. at least one) of the grammatical objects of the article. By way of example "an analogue" means one analogue or more than one analogue.

As used herein the term "analogue(s)" refers to chemical compounds that are structurally similar to another but which differ slightly in composition (as in the replacement of one atom by another or in the presence or absence of a particular functional group).

In particular, the term "39-desmethoxyrapamycin analogue" refers to a 39-desmethoxyrapamycin compound produced by the methods of WO 2004/007709 and/or as shown by formula (II). These compounds are also referred to as "parent compounds" and these terms are used interchangeably in the present application. In the present application the term "39-desmethoxyrapamycin analogue" includes reference to 39-desmethoxyrapamycin itself.

As used herein the term "derivative(s)" refers to chemical compounds that have been modified from their parent compound by semi-synthetic organic chemistry.

In particular, the term "39-desmethoxyrapamycin derivative" refers to a 39-desmethoxyrapamycin derivative according to formula (I) above, or a pharmaceutically acceptable salt thereof, produced by semi-synthetic alteration of a 39-desmethoxyrapamycin analogue. These compounds are also referred to as "compounds of the invention" or "39-desmethoxy derivatives of rapamycin" and these terms are used interchangeably in the present application.

As used herein, the term "autoimmune disorder(s)" includes, without limitation: systemic lupus erythrematosis (SLE), rheumatoid arthritis, myasthenia gravis and multiple sclerosis.

As used herein, the term "diseases of inflammation" includes, without limitation: psoriasis, dermatitis, eczema, seborrhoea, inflammatory bowel disease (including but not limited to ulcerative colitis and Crohn's disease), pulmonary inflammation (including asthma, chronic obstructive pulmonary disease, emphysema, acute respiratory distress syndrome and bronchitis), rheumatoid arthritis and eye uveitis.

As used herein, the term "cancer" refers to malignant growth of cells in skin or in body organs, for example but without limitation, breast, prostate, lung, kidney, pancreas, stomach or bowel. A cancer tends to infiltrate into adjacent tissue and spread (metastasise) to distant organs, for example to bone, liver, lung or the brain. As used herein the term cancer includes both metastatic tumour cell types, such as but not limited to, melanoma, lymphoma, leukaemia, fibrosarcoma, rhabdomyosarcoma, and mastocytoma and types of tissue carcinoma, such as but not limited to, colorectal cancer, prostate cancer, small cell lung cancer and non-small cell lung cancer, breast cancer, pancreatic cancer, bladder cancer, renal cancer, gastric cancer, glioblastoma, primary liver cancer and ovarian cancer.

As used herein the term "B-cell malignancies" includes a group of disorders that include chronic lymphocytic leukaemia (CLL), multiple myeloma, and non-Hodgkin's lymphoma (NHL). They are neoplastic diseases of the blood and blood forming organs. They cause bone marrow and immune system dysfunction, which renders the host highly susceptible to infection and bleeding.

As used herein, the term "vascular disease" includes, without limitation: hyperproliferative vascular disorders (e.g. restenosis and vascular occlusion), graft vascular atherosclerosis, cardiovascular disease, cerebral vascular disease and peripheral vascular disease (e.g. coronary artery disease, arteriosclerosis, atherosclerosis, nonatheromatous arteriosclerosis or vascular wall damage).

As used herein the terms "neuronal regeneration" refers to the stimulation of neuronal cell growth and includes neurite outgrowth and functional recovery of neuronal cells. Diseases and disorders where neuronal regeneration may be of significant therapeutic benefit include, but are not limited to, Alzheimer's disease, Parkinson's disease, Huntington's chorea, amyotrophic lateral sclerosis, trigeminal neuralgia, glossopharyngeal neuralgia. Bell's palsy, muscular dystrophy, stroke, progressive muscular atrophy, progressive bulbar inherited muscular atrophy, cervical spondylosis, Gullain-Barre syndrome, dementia, peripheral neuropathies and peripheral nerve damage, whether caused by physical injury (e.g. spinal cord injury or trauma, sciatic or facial nerve lesion or injury) or a disease state (e.g. diabetes).

As used herein the term "fibrotic diseases" refers to diseases associated with the excess production of the extracellular matrix and includes (without limitation) sarcoidosis, keloids, glomerulonephritis, end stage renal disease, liver fibrosis (including but not limited to cirrhosis, alcohol liver disease and steato-heptatitis), chronic graft nephropathy, surgical adhesions, vasculopathy, cardiac fibrosis, pulmonary fibrosis (including but not limited to idiopathic pulmonary fibrosis and cryptogenic fibrosing alveolitis), macular degeneration, retinal and vitreal retinopathy and chemotherapy or radiation-induced fibrosis.

As used herein, the term "graft vs. host disease" refers to a complication that is observed after allogeneic stem cell/bone marrow transplant. It occurs when infection-fighting cells from the donor recognize the patient's body as being different or foreign. These infection-fighting cells then attack tissues in the patient's body just as if they were attacking an infection. Graft vs. host disease is categorized as acute when it occurs within the first 100 days after transplantation and chronic if it occurs more than 100 days after transplantation. Tissues typically involved include the liver, gastrointestinal tract and skin. Chronic graft vs. host disease occurs approximately in 10-40 percent of patients after stem cell/bone marrow transplant.

As used herein, the term "bioavailability" refers to the degree to which or rate at which a drug or other substance is absorbed or becomes available at the site of biological activity after administration. This property is dependent upon a number of factors including the solubility of the compound, rate of absorption in the gut, the extent of protein binding and metabolism etc. Various tests for bioavailability that would be familiar to a person of skill in the art are described herein (see also Trepanier et al, 1998, Gallant-Haidner et al, 2000).

The term "water solubility" as used in this application refers to solubility in aqueous media, e.g. phosphate buffered saline (PBS) at pH 7.4.

The pharmaceutically acceptable salts of compounds of the invention such as the compounds of formula (I) include conventional salts formed from pharmaceutically acceptable inorganic or organic acids or bases as well as quaternary ammonium acid addition salts. More specific examples of suitable acid salts include hydrochloric, hydrobromic, sulfuric, phosphoric, nitric, perchloric, fumaric, acetic, propionic, succinic, glycolic, formic, lactic, maleic, tartaric, citric, palmoic, malonic, hydroxymaleic, phenylacetic, glutamic, benzoic, salicylic, fumaric, toluenesulfonic, methanesulfonic, naphthalene-2-sulfonic, benzenesulfonic hydroxynaphthoic, hydroiodic, malic, steroic, tannic and the like. Other acids such as oxalic, while not in themselves pharmaceutically acceptable, may be useful in the preparation of salts useful as intermediates in obtaining the compounds of the invention and their pharmaceutically acceptable salts. More specific examples of suitable basic salts include sodium, lithium, potassium, magnesium, aluminium, calcium, zinc. N,N'-dibenzylethylenediamine, chloroprocaine, choline, diethanolamine, ethylenediamine. N-methylglucamine and procaine salts. References hereinafter to a compound according to the invention include both compounds of formula (I) and their pharmaceutically acceptable salts.

Alkyl, alkenyl and alkynyl groups may be straight chain or branched.

Examples of C1-C4 alkyl groups include methyl, ethyl, n-propyl, i-propyl and n-butyl.

Examples of C2-C4 alkenyl groups include ethenyl and 2-propenyl.

Examples of C2-4 alkynyl groups include ethynyl.

C3-C6 cycloalkyl groups refers to a cycloalkyl ring including 3-6 carbon atoms that may optionally be branched. Examples include cyclopropyl, cyclobutyl, methyl-cyclobutyl, cyclopentyl and cyclohexyl, 3 to 6 membered heteroalkyl rings containing one or more heteroatoms selected from N, O and S include rings containing one or two heteroatoms, especially one heteroatom. Examples include furan, pyran, oxetane, oxirane, piperidine, pyrrolidine, azetidine, aziridine, thiirane, thiethane, thiophene, thiopyran and morpholine.

Example optional substituents for the 3 to 6 membered heteroalkyl rings include —OH, —CH$_2$OH, NH$_2$, CH$_2$NH$_2$ and COOH. Typically the 3 to 6 membered heteroalkyl rings may be unsubstituted or substituted by 1 or 2, e.g. 1 substituent.

DESCRIPTION OF THE INVENTION

The present invention provides 39-desmethoxyrapamycin derivatives, as set out above, methods for the preparation of these compounds, intermediates thereto and methods for the use of these compounds in medicine.

Preferably $R_7$ contains 7 or fewer especially 5 or fewer carbon atoms.

$R_7$ preferably contains at least one functional group selected from —PO(OH)$_2$, —OH, —COOH and —NH$_2$, more preferably —OH, —COOH or —NH$_2$, especially —COOH and OH, most especially OH. Preferably $R_7$ contains 2 or more substituents, e.g. 2-OH groups.

Suitably X represents CH$_2$;
Suitably a represents 0.
Suitably p represents 0 or 1.
Suitably m represents 0 or 1.
Suitably q represents 0, 1 or 2.
Suitably $R_{11}$ represents H. Suitably $R_{12}$ represents H.
Suitably $R_{13}$ represents H or OH.
When p represents 1, suitably $R_{10}$ represents Me. OH or CH$_2$OH.
When p represents 1, suitably $R_{11}$ represents Me. H or CH$_2$OH.
When m and p both represent 0, suitably $R_{12}$ and $R_{13}$ both represent H, $R_{14}$ represents —(CR$_8$R$_9$)$_q$—OH where q=0 or 1 and $R_8$ and $R_9$ both represent H.

When p represents 1 and m represents 0, suitably $R_{10}$ and $R_{11}$ both represent H, $R_{12}$ represents H, $R_{13}$ represents H, OH or $NH_2$, $R_{14}$ represents —$(CR_8R_9)_q$—OH where q=0 or 1 and $R_8$ and $R_9$ both represent H.

When $R_6$ represents —$POR_{15}R_{16}$ suitably $R_{15}$ and $R_{16}$ both represent $CH_3$ or both represent $CH_2CH_3$.

Suitably $R_6$ represents the residue derived from forming an ester with hydroxyl acetic acid, 3-hydroxy-2,2-dimethylpropionic acid, 2,3-dihydroxypropionic acid, 3-hydroxy-2-hydroxymethylpropionic acid or 2,2-bis(hydroxymethyl)propionic acid.

In one example set of compounds, $R_6$ represents: $C(O)R_7$

Preferably $R_7$ is the moiety formed by condensation of the macrocyclic alcohol with an acid selected from the list consisting of hydroxyacetic acid, 3-hydroxy-2,2,dimethylpropionic acid, 2,3-dihydroxypropionic acid, 3-hydroxy-2-hydroxymethylpropionic acid and 2,2-bis(hydroxymethyl)propionic acid, especially 2,2-bis(hydroxymethyl)propionic acid.

When $R_{15}$ represents:

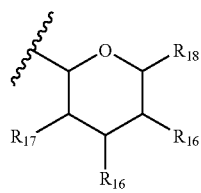

examples of this moiety include the moiety formed by forming an acetal with (i) glucose (i.e. $R_{18}$ represents $CH_2OH$ and each $R_{16}$ and $R_{17}$ represents OH), e.g. D-glucose (ii) glucosamine (i.e. $R_{18}$ represents $CH_2OH$, each $R_{16}$ represents OH and $R_{17}$ represents $NH_2$) e.g. D-glucosamine, (iii) glucuronic acid (i.e. $R_{18}$ represents COOH and each $R_{16}$ and $R_{17}$ represents OH) e.g. D-glucuronic acid and (iv) arabinose $R_{18}$ represents H and each $R_{16}$ and $R_{17}$ represents OH) e.g. D-arabinose.

When $R_{15}$ represents:

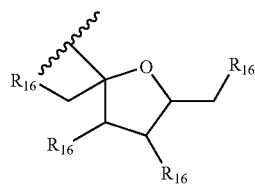

examples of this moiety include the moiety formed by forming an acetal with fructose (i.e. $R_{16}$ each represents OH), e.g. the residue of D-fructose.

When $R_{15}$ represents:

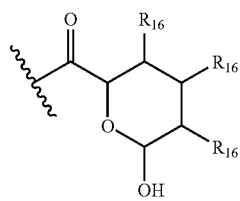

examples of this moiety include the moiety formed by forming an ester with glucuronic acid (i.e. each $R_{16}$ represents OH), e.g. the residue of D-glucuronic acid.

In general, the compounds of the invention are prepared by semi-synthetic derivatisation of a 39-desmethoxyrapamycin analogue of formula (II).

Thus a process for preparing a compound of formula (I) or a pharmaceutically acceptable salt thereof comprises:
(a) reacting a 39-desmethoxyrapamycin analogue of formula (II):

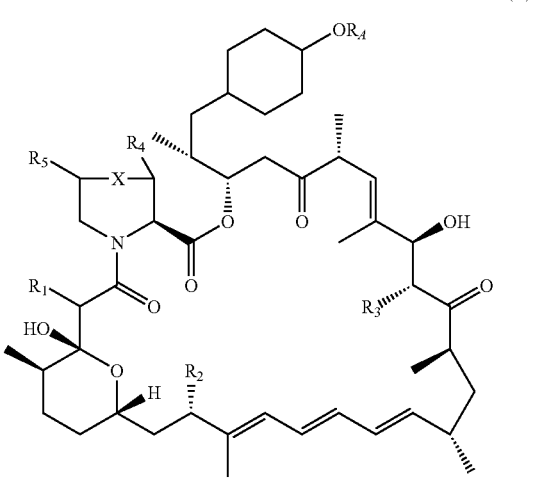

where $R_A$ represents H or $(CH_2)_2$—OH
or a protected derivative thereof, with a compound of formula (III):

$$HO-R_6 \quad (III)$$

or an activated derivative of $R_6$;
(b) converting a compound of formula (I) or a salt thereof to another compound of formula (I) or another pharmaceutically acceptable salt thereof; or
(c) deprotecting a protected compound of formula (I).

The term "activated derivative" as used above refers to (for example but without limitation): in the case of esters—carboxylic acids, acyl halides, mixed anhydrides, symmetrical anhydrides or carboxylic esters; in the case of ethers—alkyl halides, alkyl mesylates, alkyl triflates, alkyl tosylates or other suitably activated alkyl derivatives; in the case of phosphates and phosphonates—chlorophosphates, dialkyl cyanophosphates, dialkyl dialkylphosphoramidates or chlorophosphites; or in the case of acetals derived from glycosyl groups—using a glycosyl donor e.g. glycosyl halides, thioglycosides, 1-O-acyl glycosides, ortho esters, 1-O or 1-S carbonates, trichloroimidates, 4-pentenyl glycosides, glycosyl phosphate esters, 1-O-sulfonyls or 1-O-silylated glycosides.

In process (a), 39-desmethoxyrapamycin analogues of formula (II) may be prepared as described in WO 2004/007709 and as further set out in the examples herein.

In addition to the specific methods and references provided herein a person of skill in the art may also consult standard textbook references for synthetic methods, including, but not limited to Vogel's textbook of practical organic chemistry (Furniss et al., 1989) and March's advanced organic chemistry (Smith and March, 2001).

Additionally present hydroxyl groups can be protected by one of many standard hydroxy protection strategies available to one skilled in the art. Hydroxyl groups may be protected by forming ethers, including, but not limited to, substituted alkyl ethers, substituted benzyl ethers and silyl ethers. Preferably a silyl ether, including, but not limited to, trimethylsilyl, triethylsilyl, t-butyldimethylsilyl and t-butyldiphenylsilyl, ether is formed by reacting an activated form of the silane (including, but not limited to, silyl chloride or silyl triflate) with 39-desmethoxyrapamycin in the presence of a suitable base. The protecting group could then be removed by either acid hydrolysis or fluoride assisted cleavage. 1,2-Diols may be protected as acetonides, based on the condensation of an acetone derivative. This may be removed by acid catalysis.

The 39-desmethoxyrapamycin analogues of formula (II) may be used as templates for further semi-synthesis (i.e. process (a)). The pendant hydroxyl group at C-40 can be functionalised by e.g. acylation, alkylation, glycosylation or phosphorylation via a number of synthetic transformations known to a person skilled in the art.

In process (a), when $R_6$ represents a moiety of formula —C(O)$R_7$ or Y—$R_{15}$ where $R_{15}$ represents

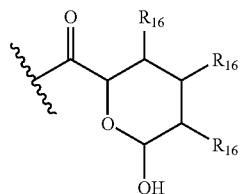

and Y=bond, the formation of a hydroxy ester, or O-acylation, can be mediated by reaction of the hydroxyl group of the compounds of formula (II) with a corresponding carboxylic acid preferably in activated form, for example a compound of formula (IIIAi) or (IIIAii):

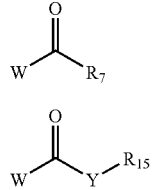

or with a compound of formula (IIIB):

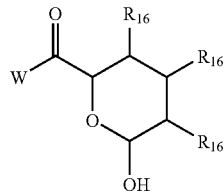

where W is a group which activates a carboxylic acid to nucleophilic attack. Carboxylic acids can be activated by the formation of for example but without limitation, acyl halides (e.g. W=Cl), mixed anhydrides (i.e. W=OC(O)R'), symmetrical anhydrides (W=OC(O)$R_7$) or carboxylic esters (i.e. W=OR').

Compounds of formula (IIIAi), (IIIAii) or (IIIB) can be prepared from their commercially available carboxylic acids using standard methods known to a person of skill in the art, and in a specific aspect compounds according to formula (IIIAi) wherein $R_7$ is —(C$R_8R_9$)$_m$(C$R_{10}R_{11}$)$_p$C$R_{12}R_{13}R_{14}$ may be prepared using methods as described in U.S. Pat. Nos. 5,362,718, 5,665,772 or EP 0 663 916.

Preferably a 39-desmethoxyrapamycin analogue is reacted in organic media with either an acid chloride or mixed anhydride in the presence of a base. Bases which may be used include, but are not limited to, pyridine, 4,4-dimethylaminopyridine (DMAP), 2,6-lutidene, 2,6-di-tert-butylpyridine, triethylamine, diisopropylethylamine, other trialkylamines, 1,8-diazabicyclo[5.4.0]undec-7-ene (DBU) or 1,5-diazabicyclo[4.3.0]non-5-ene (DBN). In specific examples described herein, 39-desmethoxyrapamycin is reacted with a mixed anhydride in the presence of DMAP.

In process (a), when $R_6$ represents a moiety of formula —C(O)$R_7$ or Y—$R_{15}$ where $R_{15}$ represents

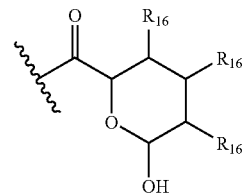

and Y=—C(O)O— or —(CH$_2$)$_2$—OC(O)O— the formation of these hydroxy esters, requires the reaction of the hydroxyl group of the compounds of formula (II) or a compound that is 40-O-(hydroxyethyl)-formula II with a reagent that will form an activated carbonate such as a compound of formula IV

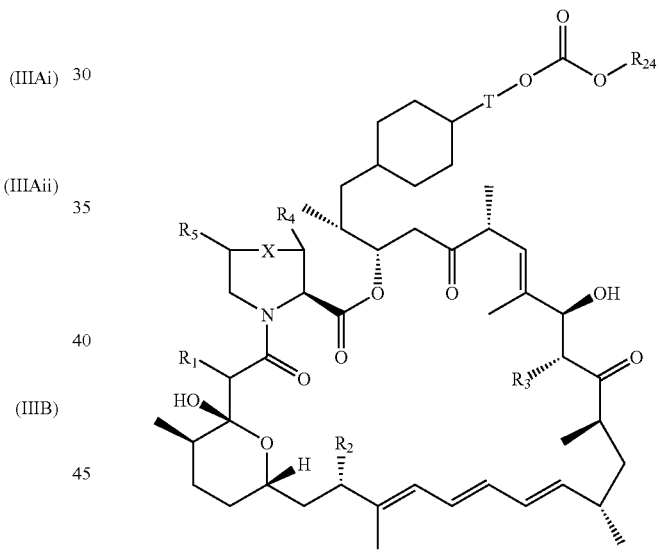

(IV), where T=bond or —O(CH$_2$)$_2$— and $R_{24}$ is an alkyl or aryl group, preferably an aryl group, especially para-nitrophenyl group.

The compound of formula IV can then react with a compound of formula III, to generate compounds with $R_6$ attached to the 40-hydroxyl group, or 40-O-(hydroxyethyl) group via a carbonate linker (WO 2004/101583).

Likewise a 39-desmethoxyrapamycin analogue may be derivatised with different hydroxy ethers at C-40, by reacting the 39-desmethoxyrapamycin analogue with a suitably activated alkyl derivative of choice, to form a 40-O-alkyl-39-desmethoxyrapamycin derivative. Activated alkyl groups refers to an alkyl group that has been activated by one of many methods, including, but not limited to, formation of alkyl halides (RCl, RI, RBr), alkyl mesylates (ROS(O)$_2$CH$_3$), alkyl triflates (ROS(O)$_2$CF$_3$), alkyl tosylates (ROS(O)$_2$PhMe). The activated alkyl group would then be reacted with a 39-desmethoxyrapamycin analogue in organic media in the presence of a suitable base. Standard methods to optimise the reaction conditions may be employed by a person of skill in the art to avoid alkylation at other reactive positions.

Likewise a 39-desmethoxyrapamycin analogue may be phosphorylated, and after deprotection of the phosphate esters it can yield a 40-O-phospho-39-desmethoxyrapamycin derivative or a 40-O-dialkylphospho-39-desmethoxyrapamycin derivative, and salts of these derivatives made by methods known to one skilled in the art. Phosphate esters can be formed directly, or indirectly via an O-phosphite (i.e. (R'O)$_2$POR) in which the trivalent phosphite is oxidised (preferably by the action of a peracid, such as but not limited not mCPBA) to the pentavalent phosphate. Direct phosphorylation methods include, but are not limited to, reaction of a 39-desmethoxyrapamycin analogue with a protected chlorophosphate (e.g. (BnO)$_2$P(O)Cl, (Alkyl(O)$_2$P(O)Cl), preferably in the presence of DMAP in organic media, or reaction of a 39-desmethoxyrapamycin analogue with phosphorus oxychloride (POCl$_3$), in the presence of a base such as triethylamine, followed by acid hydrolysis of the resultant O-dichlorophosphate (i.e. ROP(O)Cl$_2$), or coupling to a dialkyl cyanophosphate (WO 01/81355). Dialkyl or diaryl chlorophosphate may be generated in situ by the reaction of a dialkyl or diaryl phosphite (i.e. (RO)$_2$P(O)H) with carbon tetrachloride in the presence of base. Methods of forming the O-phosphite (for oxidation to the O-phosphate) include, but are not limited to, coupling a 39-desmethoxyrapamycin analogue with a dialkyl dialkylphosphoramidate (preferably dialkyl diisopropylphosphorylamidate), in the presence of base (preferably tetrazole), or coupling using a chlorophosphite in the presence of base (Evans et al., 1992). The choice of protecting group is important, ethyl and methyl esters of phosphates are not readily hydrolysable under acidic or basic conditions. Preferably the protecting groups include, but are not limited to, benzyl esters (cleaved via sodium iodide/chlorotrimethylsilane promoted hydrolysis, (WO 01/81355)) or 2-cyanoethyl esters (cleaved via mild base catalysed cleavage). Similarly 40-O-dialkylphosphono-39-desmethoxyrapamycin derivatives can be generated by reacting a 39-desmethoxyrapamycin analogue with a suitable activated (as described above) dialkylphosphonate or dialkylphosphite.

In process (a), when $R_{15}$ represents a moiety of formula

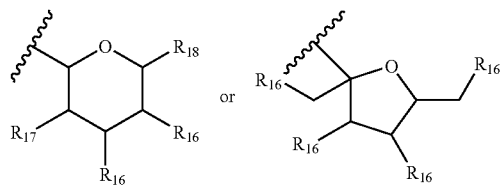

the formation of a glycosidic linkage, or O-glycosylation, can be mediated by reaction of the hydroxyl group with a corresponding glycosyl donor, preferably in activated form, (see Toshima and Tatsuta (1993)) for example a compound of formula (IIIC):

or a compound of formula (IIID):

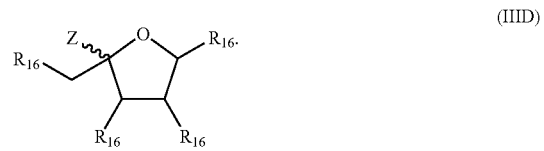

Using a 'glycosyl donor', including, but not limited to, glycosyl halides (Z=F, Cl, Br), thioglycosides (Z=SMe, Set, SPh, SPy, SCN), 1-O-acyl glycosides (Z=OC(O)R), ortho esters (Z=OC(Me)(R)(O—C2 of formula (IIIC/IIID)), 1-O or 1-S carbonates (Z=OC(S)SMe, Z=OC(O)imidazole, Z=OC(S)imidazole, Z=SC(S)OEt), trichloroimidates (Z=OC(=NH)CCl$_3$), 4-pentenyl glycosides (Z=OCH$_2$CH$_2$CH$_2$CH=CH$_2$), phosphate esters (e.g. Z=OP(O)(OPh)$_2$), 1-O-sulfonyls (Z=tosyl), or 1-O-silylated glycosides (Z=OTMS or OTBS), the 39-desmethoxyrapamycin analogue may be glycosylated in organic media, preferentially in the presence of an activator (such as a Lewis acid or heavy metal salt, see Toshima and Tatsuta, 1993)). The specific glycosyl donor used and the reaction conditions will determine whether an alpha or beta glycoside is formed. As before for acylation, any hydroxyl groups present in the parent compound may be protected or masked such that using one equivalent of glycosyl donor will result in 40-O-acylation. The remaining hydroxyls on the glycosyl donor should be protected, as e.g. O-acetates, O-benzoates, 1,2-acetonides, so a further deprotection will be necessary. Furthermore 2-deoxyglycosyl donors such as glycals may be used (a reductive step is also required) to prepare 2'-deoxy-39-desmethoxyrapamycin glycosides and 2,6-dideoxyglycosyl donors such as 2,6-anhydro-2-thiosugars may be used to prepare 2',6'-dideoxy-39-desmethoxyrapamycin glycosides.

In process (b), salt formation and exchange may be performed by conventional methods known to a person of skill in the art. Interconversions of compounds of formula (I) may be performed by known processes for example hydroxy and keto groups may be interconverted by oxidation/reduction as described elsewhere herein. Compounds of formula (I) in which $R_6$ represents —PO(OH)$_2$ may be prepared by phosphorylating a corresponding compound of formula (I) in which $R_6$ represents OH. Suitable conditions are provided elsewhere herein.

In processes (a) and (c), examples of protecting groups and the means for their removal can be found in T W Greene "Protective Groups in Organic Synthesis" (J Wiley and Sons, 1991). Suitable hydroxyl protecting groups include alkyl (e.g. methyl), acetal (e.g. acetonide) and acyl (e.g. acetyl or benzoyl) which may be removed by hydrolysis, and arylalkyl (e.g. benzyl) which may be removed by catalytic hydrolysis, or silyl ether, which may be removed by acidic hydrolysis or fluoride ion assisted cleavage.

In addition to process (a), 39-desmethoxyrapamycin analogues of formula (I) where $R_6$ represents $R_7$ can be synthesised by Lipase catalysed transesterification. For example, but without limitation, a 39-desmethoxyrapamycin analogue of formula (II) can be reacted with a vinyl ester of formula (V) in the presence of lipase PS-C "Amano" II under the reaction conditions described by Gu et al (2005) and as further set out in the examples herein. This methodology is not limited to the use of vinyl esters and the transesterification may be catalysed by other lipases or esterases.

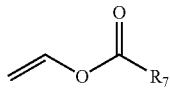 (V)

Other compounds of the invention may be prepared by methods known per se or by methods analogous to those described above.

The novel 39-desmethoxyrapamycin derivatives are useful directly, and as templates for further semi-synthesis or bioconversion, to produce compounds useful as immunosuppressants, antifungal agents, anticancer agents, anti-inflammatory agents, neuroregenerative agents or agents for the treatment of transplantation rejection, graft vs. host disease, autoimmune disorders, vascular disease and/or fibrotic diseases. Methods for the semisynthetic derivatisation of rapamycin and analogues thereof are well known in the art and include (but are not limited to) those modifications described in e.g. U.S. Pat. Nos. 5,665,772; 5,362,718, WO 96/41807; U.S. Pat. Nos. 5,728,710, 5,378,836; 5,138,051; 5,665,772, 5,391,730; 5,023,262, 5,563,145, 5,446,048, 5,912,253, 5,221,670; 5,955,457; WO 98/04279, U.S. Pat. Nos. 6,015,815 and 5,432,183.

The above structures of intermediates (e.g. compounds of formula (II) may be subject to tautomerisation and where a representative tautomer is illustrated it will be understood that all tautomers for example keto compounds where enol compounds are illustrated and vice versa are intended to be referred to.

In a further aspect, the present invention provides the use of the 39-desmethoxyrapamycin derivatives of the invention in medicine. In a further aspect the present invention provides for the use of 39-desmethoxyrapamycin derivatives of the invention in the preparation of a medicament for the induction or maintenance of immunosuppression, the stimulation of neuronal regeneration or the treatment of cancer, B-cell malignancies, fungal infections, transplantation rejection, graft vs. host disease, autoimmune disorders, diseases of inflammation vascular disease and fibrotic diseases or agents for use in the regulation of wound healing.

Multi-Drug Resistance (MDR) is a significant problem in the treatment of cancer and B-cell malignancies. It is the principle reason behind the development of drug resistance in many cancers (Persidis A, 1999). MDR is associated with increased level of adenosine triphosphate binding cassette transporters (ABC transporters), in particular an increase in the expression of the MDR1 gene which encodes for P-glycoprotein (P-gp) or the MRP1 gene which encodes MRP1. The level of MDR1 gene expression varies widely across different cancer-derived cell lines, in some cell lines it is undetectable, whereas in others may show up to a 10 or 100-fold increased expression relative to standard controls.

Therefore, a further aspect of the invention provides for the use of a 39-desmethoxyrapamycin derivative of the invention in the treatment of MDR cancers or B-cell malignancies. In a specific aspect the present invention provides for the use of 39-desmethoxyrapamycin derivatives in the treatment of P-gp-expressing cancers or B-cell malignancies. In a yet more preferred embodiment the present invention provides for the use of a 39-desmethoxyrapamycin derivative of the invention in the treatment of high P-gp expressing cancers or B-cell malignancies. Particularly, high P-gp expressing cancers or B-cell malignancies may have 2-fold, 5-fold, 10-fold, 20-fold, 25-fold, 50-fold or 100-fold increased expression relative to control levels. Suitable controls are cells which do not express P-gp, which have a low expression level of P-gp or which have low MDR function, a person of skill in the art is aware of or can identify such cell lines; by way of example (but without limitation) suitable cell lines include: MDA435/LCC6, SBC-3/CDDP, MCF7, NCI-H23, NCI-H522, A549/ATCC, EKVX, NCI-H226, NCI-H322M, NCI-H460, HOP-18, HOP-92, LXFL 529, DMS 114, DMS 273, HT29, HCC-2998, HCT-116, COLO 205, KM12, KM20L2, MDA-MB-231/ATCC, MDA-MB-435, MDA-N, BT-549, T-47D, OVCAR-3, OVCAR-4, OVCAR-5, OVCAR-8, IGROV1, SK-OV-3, K-562, MOLT-4, HL-60(TB), RPMI-8226, SR, SN12C, RXF-631, 786-0, TK-10, LOX IMVI, MALME-3M, SK-MEL-2, SK-MEL-5, SK-MEL-28, M14, UACC-62, UACC-257, PC-3, DU-145, SNB-19, SNB-75, SNB-78, U251, SF-268, SF-539, XF 498.

In an alternative aspect the present invention provides for the use of a 39-desmethoxyrapamycin derivative of the invention in the preparation of a medicament for use in the treatment of MDR cancers or B-cell malignancies. In a specific aspect the present invention provides for the use of a 39-desmethoxyrapamycin derivative of the invention in the preparation of a medicament for use in the treatment of P-gp-expressing cancers or B-cell malignancies. In a yet more preferred embodiment the present invention provides for the use of a 39-desmethoxyrapamycin derivative in the preparation of a medicament for use in the treatment of high P-gp expressing cancers or B-cell malignancies. Particularly, high P-gp expressing cancers or B-cell malignancies may have 2-fold, 5-fold, 10-fold, 20-fold, 25-fold, 50-fold or 100-fold increased expression relative to control levels. Suitable controls are described above.

Methods for determining the expression level of P-gp in a sample are discussed further herein.

Therefore, in a further aspect the present invention provides a method for the treatment of P-gp-expressing-cancers or B-cell malignancies comprising administering a therapeutically effective amount of a 39-desmethoxyrapamycin derivative of the invention. The expression level of P-glycoprotein (P-gp) in a particular cancer type may be determined by a person of skill in the art using techniques including but not limited to real time RT-PCR (Szakács et al, 2004; Stein et al, 2002; Langmann et al; 2003. Alvarez et al, 1995. Boyd et al, 1995), by immunohistochemistry (Stein et al, 2002) or using microarrays (Lee et al, 2003), these methods are provided as examples only, other suitable methods will occur to a person of skill in the art.

One skilled in the art would be able by routine experimentation to determine the ability of these compounds to inhibit fungal growth (e.g. Baker, H., et al., 1978; NCCLS Reference method for broth dilution antifungal susceptibility testing for yeasts: Approved standard M27-A, 17(9). 1997). Additionally, one skilled in the art would be able by routine experimentation to determine the ability of these compounds to inhibit tumour cell growth, (see Dudkin, L. et al., 2001; Yu et al. 2001). In a further aspect the compounds of this invention are useful for inducing immunosuppression, assays for determining a compound's efficacy in these areas are well known to those of skill in the art, for example but without limitation: Immunosuppressant activity—Warner, L. M., et al., 1992, Kahan et al. (1991) & Kahan & Camardo, 2001); Allografts—Fishbein, T. M., et al., 2002, Kirchner et al. 2000; Autoimmune/Inflammatory/Asthma—Carlson, R. P. et al., 1993, Powell, N. et al., 2001; Diabetes I—Rabinovitch, A. et al., 2002; Psoriasis—Reitamo, S. et al., 2001; Rheumatoid arthritis—Foey, A., et al., 2002; Fibrosis—Zhu, J. et al., 1999, Jain, S., et al., 2001. Gregory et al. 1993.

The ability of the 39-desmethoxyrapamycin derivatives of the invention to induce immunosuppression may be demonstrated in standard tests used for this purpose. In a further aspect the 39-desmethoxyrapamycin derivatives of this invention are useful in relation to antifibrotic, neuroregenerative and anti-angiogenic mechanisms, one skilled in the art would be able by routine experimentation to determine the ability of these compounds to prevent angiogenesis (e.g. Guba, M., et al., 2002). One of skill in the art would be able by routine experimentation to determine the utility of these compounds to treat vascular hyperproliferative disease, for example in drug-eluting stents (e.g. Morice, M. C., et al., 2002). Additionally, one of skill in the art would be able by routine experimentation to determine the neuroregenerative ability of these compounds (e.g. Myckatyn, T. M., et al., 2002, Steiner et al. 1997).

The present invention also provides a pharmaceutical composition comprising a 39-desmethoxyrapamycin derivative of the invention, together with a pharmaceutically acceptable carrier.

Rapamycin and related compounds that are or have been in clinical trials, such as CCI-779 and RAD001 have poor pharmacological profiles, poor water solubility and poor bioavailability. The present invention provides 39-desmethoxyrapamycin derivatives which have improved properties such as improved stability and/or increased cell membrane permeability. A person of skill in the art will be able to readily determine the solubility of a given compound of the invention using standard methods. A representative method is shown in the examples herein.

Additionally, a person of skill in the art will be able to determine the pharmacokinetics and bioavailability of a compound of the invention using in vivo and in vitro methods known to a person of skill in the art, including but not limited to those described below and in the examples, alternative assays are well known to a person of skill in the art including but not limited to those described below and in Gallant-Haidner et al, 2000 and Trepanier et al, 1998 and references therein. The bioavailability of a compound is determined by a number of factors, (e.g. water solubility, rate of absorption in the gut, the extent of protein binding and metabolism) each of which may be determined by in vitro tests as described below, it will be appreciated by a person of skill in the art that an improvement in one or more of these factors will lead to an improvement in the bioavailability of a compound. Alternatively, the bioavailability of a compound may be measured using in vivo methods as described in more detail below.

Caco-2 Permeation Assay

Confluent Caco-2 cells (Li, A. P., 1992; Grass, G. M., et al., 1992, Volpe, D. A., et al., 2001) in a 24 well Corning Costar Transwell format may be used, e.g. as provided by In Vitro Technologies Inc. (IVT Inc., Baltimore, Md., USA). The apical chamber contains 0.15 mL Hank's balanced buffer solution (HBBS) pH 7.4, 1% DMSO, 0.1 mM Lucifer Yellow. The basal chamber contains 0.6 mL HBBS pH 7.4, 1% DMSO. Controls and tests are then incubated at 37° C. in a humidified incubator and shaken at 130 rpm for 1 h. Lucifer Yellow permeates via the paracellular (between the tight junctions) route only, a high Apparent Permeability ($P_{app}$) for Lucifer Yellow indicates cellular damage during assay and all such wells were rejected. Propranolol (good passive permeation with no known transporter effects) & acebutalol (poor passive permeation attenuated by active efflux by P-glycoprotein) are used as reference compounds. Compounds may be tested in a uni- and bi-directional format by applying compound to the apical or basal chamber (at 0.01 mM). Compounds in the apical or basal chambers are analysed by HPLC-MS. Results are expressed as Apparent Permeability, $P_{app}$, (nm/s) and as the Flux Ratio (A to B versus B to A).

$$Papp\ (nm/s) = \frac{\text{Volume Acceptor}}{\text{Area} \times [\text{donor}]} \times \frac{\Delta[\text{acceptor}]}{\Delta \text{time}}$$

Volume Acceptor: 0.6 mL (A>B) and 0.15 mL (B>A)
Area of monolayer: 0.33 cm$^2$
$\Delta$time: 60 min A positive value for the Flux Ratio indicates active efflux from the apical surface of the cells.

Human Liver Microsomal (HLM) Stability Assay

Liver homogenates provide a measure of a compounds inherent vulnerability to Phase I (oxidative) enzymes, including CYP450s (e.g. CYP2C8, CYP2D6, CYP1A, CYP3A4, CYP2E1), esterases, amidases and flavin monooxygenases (FMOs).

The half life (T1/2) of test compounds can be determined, on exposure to Human Liver Microsomes, by monitoring their disappearance over time by LC-MS. Compounds at 0.001 mM are incubated at for 40 min at 37° C., 0.1 M Tris-HCl, pH 7.4 with human microsomal sub-cellular fraction of liver at 0.25 mg/mL protein and saturating levels of NADPH as co-factor. At timed intervals, acetonitrile is added to test samples to precipitate protein and stop metabolism. Samples are centrifuged and analysed for parent compound by HPLC-MS.

In Vivo Bioavailability Assays

In vivo assays may also be used to measure the bioavailability of a compound (see e.g. Crowe et al, 1999). Generally, a compound is administered to a test animal (e.g. mouse or rat) both intraperitoneally (i.p.) or intravenously (i.v.) and orally (p.o.) and blood samples are taken at regular intervals to examine how the plasma concentration of the drug varies over time. The time course of plasma concentration over time can be used to calculate the absolute bioavailability of the compound as a percentage using standard models. An example of a typical protocol is described below.

Mice are dosed with 3 mg/kg of the compound of the invention or the parent compound i.v. or 10 mg/kg of a compound of the invention of the parent compound p.o. Blood samples are taken at 5 minute, 15 minute, 1 h, 4 h and 24 h intervals and the concentration of the compound of the invention or parent compound in the sample is determined via HPLC. The time-course of plasma concentrations can then be used to derive key parameters such as the area under the plasma concentration-time curve (AUC—which is directly proportional to the total amount of unchanged drug that reaches the systemic circulation), the maximum (peak) plasma drug concentration, the time at which maximum plasma drug concentration occurs (peak time), additional factors which are used in the accurate determination of bioavailability include: the compound's terminal half life, total body clearance, steady-state volume of distribution and F %. These parameters are then analysed by non-compartmental or compartmental methods to give a calculated percentage bioavailability, for an example of this type of method see Gallant-Haidner et al, 2000 and Trepanier et al, 1998 and references therein, and references therein.

The aforementioned 39-desmethoxyrapamycin derivatives of the invention or a formulation thereof may be administered by any conventional method for example but without limitation they may be administered parenterally, orally, topically (including buccal, sublingual or transdermal), via a medical device (e.g. a stent), by inhalation or via injection (subcutaneous or intramuscular). The treatment may consist of a single dose or a plurality of doses over a period of time.

Whilst it is possible for a compound of the invention to be administered alone, it is preferable to present it as a pharmaceutical formulation, together with one or more acceptable carriers. The carrier(s) must be "acceptable" in the sense of being compatible with the compound of the invention and not deleterious to the recipients thereof. Examples of suitable carriers are described in more detail below.

The 39-desmethoxyrapamycin derivatives of the invention may be administered alone or in combination with other therapeutic agents, co-administration of two (or more) agents allows for significantly lower doses of each to be used, thereby reducing the side effects seen.

In one embodiment, a 39-desmethoxyrapamycin derivative is co-administered with another therapeutic agent for the induction or maintenance of immunosuppression, for the treatment of transplantation rejection, graft vs. host disease, autoimmune disorders or diseases of inflammation preferred agents include, but are not limited to, immunoregulatory agents e.g. azathioprine, corticosteroids, cyclophosphamide, cyclosporin A, FK506, Mycophenolate Mofetil, OKT-3 and ATG.

In an alternative embodiment, a 39-desmethoxyrapamycin derivative is co-administered with another therapeutic agent for the treatment of cancer or B-cell malignancies preferred agents include, but are not limited to, methotrexate, leukovorin, adriamycin, prenisone, bleomycin, cyclophosphamide, 5-fluorouracil, paclitaxel, docetaxel, vincristine, vinblastine, vinorelbine, doxorubicin, tamoxifen, toremifene, megestrol acetate, anastrozole, goserelin, anti-HER2 monoclonal antibody (e.g. Herceptin™), capecitabine, raloxifene hydrochloride, EGFR inhibitors (e.g. Iressa®, Tarceva™, Erbitux™), VEGF inhibitors (e.g. Avastin™), proteasome inhibitors (e.g. Velcade™), Glivec® D or hsp90 inhibitors (e.g. 17-AAG). Additionally, a 39-desmethoxyrapamycin derivative may be administered in combination with other therapies including, but not limited to, radiotherapy or surgery.

In one embodiment, a 39-desmethoxyrapamycin derivative is co-administered with another therapeutic agent for the treatment of vascular disease, preferred agents include, but are not limited to, ACE inhibitors, angiotensin II receptor antagonists, fibric acid derivatives. HMG-CoA reductase inhibitors, beta adrenergic blocking agents, calcium channel blockers, antioxidants, anticoagulants and platelet inhibitors (e.g. Plavix™).

In one embodiment, a 39-desmethoxyrapamycin derivative is co-administered with another therapeutic agent for the stimulation of neuronal regeneration, preferred agents include, but are not limited to, neurotrophic factors e.g. nerve growth factor, glial derived growth factor, brain derived growth factor, ciliary neurotrophic factor and neurotrophin-3.

In one embodiment, a 39-desmethoxyrapamycin derivative is co-administered with another therapeutic agent for the treatment of fungal infections; preferred agents include, but are not limited to, amphotericin B, flucytosine, echinocandins (e.g. caspofungin, anidulafungin or micafungin), griseofulvin, an imidazole or a triazole antifungal agent (e.g. clotrimazole, miconazole, ketoconazole, econazole, butoconazole, oxiconazole, terconazole, itraconazole, fluconazole or voriconazole).

By co-administration is included any means of delivering two or more therapeutic agents to the patient as part of the same treatment regime, as will be apparent to the skilled person. Whilst the two or more agents may be administered simultaneously in a single formulation this is not essential. The agents may administered in different formulations and at different times.

The formulations may conveniently be presented in unit dosage form and may be prepared by any of the methods well known in the art of pharmacy. Such methods include the step of bringing into association the active ingredient (compound of the invention) with the carrier which constitutes one or more accessory ingredients. In general the formulations are prepared by uniformly and intimately bringing into association the active ingredient with liquid carriers or finely divided solid carriers or both, and then, if necessary, shaping the product.

The 39-desmethoxyrapamycin derivatives of the invention will normally be administered orally or by any parenteral route, in the form of a pharmaceutical formulation comprising the active ingredient, optionally in the form of a non-toxic organic, or inorganic, acid, or base, addition salt, in a pharmaceutically acceptable dosage form. Depending upon the disorder and patient to be treated, as well as the route of administration, the compositions may be administered at varying doses.

For example, the compounds of the invention can be administered orally, buccally or sublingually in the form of tablets, capsules, ovules, elixirs, solutions or suspensions, which may contain flavouring or colouring agents, for immediate-, delayed- or controlled-release applications.

Solutions or suspensions of 39-desmethoxyrapamycin derivatives suitable for oral administration may also contain excipients e.g. N,N-dimethylacetamide, dispersants e.g. polysorbate 80, surfactants, and solubilisers, e.g. polyethylene glycol. Phosal 50 PG (which consists of phosphatidylcholine, soya-fatty acids, ethanol, mono/diglycerides, propylene glycol and ascorbyl palmitate), Such tablets may contain excipients such as microcrystalline cellulose, lactose (e.g. lactose monohydrate or lactose anyhydrous), sodium citrate, calcium carbonate, dibasic calcium phosphate and glycine, disintegrants such as starch (preferably corn, potato or tapioca starch), sodium starch glycollate, croscarmellose sodium and certain complex silicates, and granulation binders such as polyvinylpyrrolidone, hydroxypropylmethylcellulose (HPMC), hydroxy-propylcellulose (HPC), macrogol 8000, sucrose, gelatin and acacia. Additionally, lubricating agents such as magnesium stearate, stearic acid, glyceryl behenate and talc may be included.

Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the compounds of the invention may be combined with various sweetening or flavouring agents, colouring matter or dyes, with emulsifying and/or suspending agents and with diluents such as water, ethanol, propylene glycol and glycerin, and combinations thereof.

A tablet may be made by compression or moulding, optionally with one or more accessory ingredients. Compressed tablets may be prepared by compressing in a suitable machine the active ingredient in a free-flowing form such as a powder or granules, optionally mixed with a binder (e.g. povidone, gelatin, hydroxypropylmethyl cellulose), lubricant, inert diluent, preservative, disintegrant (e.g. sodium starch glycolate, cross-linked povidone, cross-linked sodium carboxymethyl cellulose), surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethylcellulose in varying proportions to provide desired release profile.

Formulations in accordance with the present invention suitable for oral administration may be presented as discrete units such as capsules, cachets or tablets, each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

Formulations suitable for topical administration in the mouth include lozenges comprising the active ingredient in a flavoured basis, usually sucrose and acacia or tragacanth; pastilles comprising the active ingredient in an inert basis such as gelatin and glycerin, or sucrose and acacia; and mouth-washes comprising the active ingredient in a suitable liquid carrier.

It should be understood that in addition to the ingredients particularly mentioned above the formulations of this invention may include other agents conventional in the art having regard to the type of formulation in question, for example those suitable for oral administration may include flavouring agents.

Pharmaceutical compositions adapted for topical administration may be formulated as ointments, creams, suspensions, lotions, powders, solutions, pastes, gels, impregnated dressings, sprays, aerosols or oils, transdermal devices, dusting powders, and the like. These compositions may be prepared via conventional methods containing the active agent. Thus, they may also comprise compatible conventional carriers and additives, such as preservatives, solvents to assist drug penetration, emollient in creams or ointments and ethanol or oleyl alcohol for lotions. Such carriers may be present as from about 1% up to about 98% of the composition. More usually they will form up to about 80% of the composition. As an illustration only, a cream or ointment is prepared by mixing sufficient quantities of hydrophilic material and water, containing from about 5-10% by weight of the compound, in sufficient quantities to produce a cream or ointment having the desired consistency.

Pharmaceutical compositions adapted for transdermal administration may be presented as discrete patches intended to remain in intimate contact with the epidermis of the recipient for a prolonged period of time. For example, the active agent may be delivered from the patch by iontophoresis.

For applications to external tissues, for example the mouth and skin, the compositions are preferably applied as a topical ointment or cream. When formulated in an ointment, the active agent may be employed with either a paraffinic or a water-miscible ointment base.

Alternatively, the active agent may be formulated in a cream with an oil-in-water cream base or a water-in-oil base.

For parenteral administration, fluid unit dosage forms are prepared utilizing the active ingredient and a sterile vehicle, for example but without limitation water, alcohols, polyols, glycerine and vegetable oils, water being preferred. The active ingredient, depending on the vehicle and concentration used, can be either suspended or dissolved in the vehicle. In preparing solutions the active ingredient can be dissolved in water for injection and filter sterilised before filling into a suitable vial or ampoule and sealing.

Advantageously, agents such as local anaesthetics, preservatives and buffering agents can be dissolved in the vehicle. To enhance the stability, the composition can be frozen after filling into the vial and the water removed under vacuum. The dry lyophilized powder is then sealed in the vial and an accompanying vial of water for injection may be supplied to reconstitute the liquid prior to use.

Parenteral suspensions are prepared in substantially the same manner as solutions, except that the active ingredient is suspended in the vehicle instead of being dissolved and sterilization cannot be accomplished by filtration. The active ingredient can be sterilised by exposure to ethylene oxide before suspending in the sterile vehicle. Advantageously, a surfactant or wetting agent is included in the composition to facilitate uniform distribution of the active ingredient.

The compounds of the invention may also be administered using medical devices known in the art. For example, in one embodiment, a pharmaceutical composition of the invention can be administered with a needleless hypodermic injection device, such as the devices disclosed in U.S. Pat. Nos. 5,399, 163; 5,383,851; 5,312,335; 5,064,413; 4,941,880; 4,790,824; or 4,596,556. Examples of well-known implants and modules useful in the present invention include: U.S. Pat. No. 4,487, 603, which discloses an implantable micro-infusion pump for dispensing medication at a controlled rate; U.S. Pat. No. 4,486,194, which discloses a therapeutic device for administering medicaments through the skin; U.S. Pat. No. 4,447, 233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. In a specific embodiment the 39-desmethoxyrapamycin derivative may be administered using a drug-eluting stent, for example corresponding to those described in WO 01/87263 and related publications or those described by Perin (Perin, EC, 2005). Many other such implants, delivery systems, and modules are known to those skilled in the art.

The dosage to be administered of a 39-desmethoxyrapamycin derivative of the invention will vary according to the particular compound, the disease involved, the subject, and the nature and severity of the disease and the physical condition of the subject, and the selected route of administration. The appropriate dosage can be readily determined by a person skilled in the art.

The compositions may contain from 0.1% by weight, preferably from 5-60%, more preferably from 10-30% by weight, of a compound of invention, depending on the method of administration.

It will be recognized by one of skill in the art that the optimal quantity and spacing of individual dosages of a compound of the invention will be determined by the nature and extent of the condition being treated, the form, route and site of administration, and the age and condition of the particular subject being treated, and that a physician will ultimately determine appropriate dosages to be used. This dosage may be repeated as often as appropriate. If side effects develop the amount and/or frequency of the dosage can be altered or reduced, in accordance with normal clinical practice.

EXAMPLES

Figure 1:
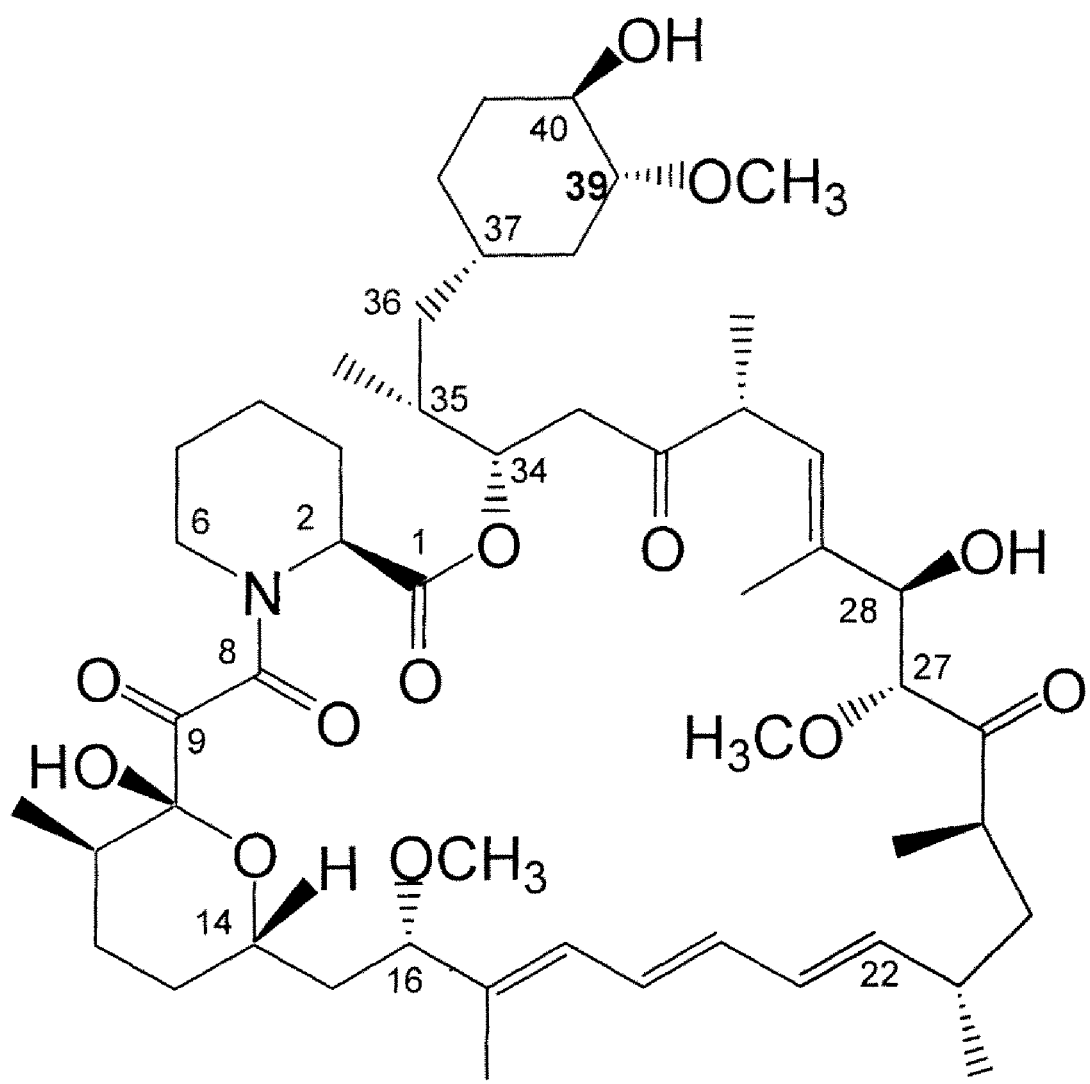
FIG. 1: shows the structure of rapamycin

General Methods and Materials
Materials

All reagents were obtained from commercial sources, and used without further purification unless stated otherwise.
Culture

*S. hygroscopicus* MG2-10 [IJMNOQLhis] (WO 04/007709; Gregory et al., 2004) was maintained on medium 1 agar plates (see below) at 28° C. Spore stocks were prepared after growth on medium 1, preserved in 20% w/v glycerol: 10% w/v lactose in distilled water and stored at −80° C. Vegetative cultures were prepared by inoculating 0.1 mL of frozen stock into 50 mL medium 2 (see below) in 250 mL flask. The culture was incubated for 36 to 48 hours at 28° C., 300 rpm.
Production Method:

Vegetative cultures were inoculated at 2.5-5% v/v into medium 3. Cultivation was carried out for 6-7 days, 26° C., 300 rpm.
Feeding Procedure:

The feeding/addition of the selected carboxylic acid was carried out 24-48 hours after inoculation and was fed at 1-2 mM unless stated otherwise.
Medium 1:

| component | Source | Catalogue # | Per L |
|---|---|---|---|
| Corn steep powder | Sigma | C-8160 | 2.5 g |
| Yeast extract | Difco | 0127-17 | 3 g |
| Calcium carbonate | Sigma | C5929 | 3 g |
| Iron sulphate | Sigma | F8633 | 0.3 g |
| BACTO agar | Difco | 2140-10 | 20 g |
| Wheat starch | Sigma | S2760 | 10 g |
| Water to | | | 1 L |

The media was then sterilised by autoclaving 121° C., 20 min.
Medium 2: RapV7 Seed Medium

| Component | Per L |
|---|---|
| Toasted Nutrisoy (ADM Ingredients Ltd) | 5 g |
| Avedex W80 dextrin (Deymer Ingredients Ltd) | 35 g |
| Corn Steep Solids (Sigma) | 4 g |
| Glucose | 10 g |
| $(NH_4)_2SO_4$ | 2 g |
| Lactic acid (80%) | 1.6 mL |
| $CaCO_3$(Caltec) | 7 g |

Adjust pH to 7.5 with 1 M NaOH.

The media was then sterilised by autoclaving 121° C., 20 min. After sterilisation 0.16 mL of 40% glucose is added to each 7 mL of media.

Medium 3: MD6 Medium (Fermentation Medium)

| Component | Per L |
|---|---|
| Toasted Nutrisoy (ADM Ingredients Ltd) | 30 g |
| Corn starch (Sigma) | 30 g |
| Avedex W80 dextrin (Deymer Ingredients Ltd) | 19 g |
| Yeast (Allinson) | 3 g |
| Corn Steep Solids (Sigma) | 1 g |
| $KH_2PO_4$ | 2.5 g |
| $K_2HPO_4$ | 2.5 g |
| $(NH_4)_2SO_4$ | 10 g |
| NaCl | 5 g |
| $CaCO_3$ (Caltec) | 10 g |
| $MnCl_2 \cdot 4H_2O$ | 10 mg |
| $MgSO_4 \cdot 7H_2O$ | 2.5 mg |
| $FeSO_4 \cdot 7H_2O$ | 120 mg |
| $ZnSO_4 \cdot 7H_2O$ | 50 mg |
| MES (2-morpholinoethane sulphuric acid monohydrate) | 21.2 g | pH is corrected to 6.0 with 1 M NaOH

Before sterilization 0.4 mL of Sigma α-amylase (BAN 250) was added to 1 L of medium.
Medium was sterilised for 20 min at 121° C.
After sterilisation 0.35 mL of sterile 40% fructose and 0.10 mL of L-lysine (140 mg/mL in water, filter-sterilised) was added to each 7 mL.
Medium 4: RapV7a Seed Medium

| Component | Per L |
|---|---|
| Toasted Nutrisoy (ADM Ingredients Ltd) | 5 g |
| Avedex W80 dextrin (Deymer Ingredients Ltd) | 35 g |
| Corn Steep Solids (Sigma) | 4 g |
| $(NH_4)_2SO_4$ | 2 g |
| Lactic acid (80%) | 1.6 mL |
| $CaCO_3$ (Caltec) | 7 g |

Adjust pH to 7.5 with 1 M NaOH.

The media was then sterilised by autoclaving 121° C., 20 min.
Medium 5: MD6/5-1 Medium (Fermentation Medium)

| Component | Per L |
|---|---|
| Toasted Nutrisoy (ADM Ingredients Ltd) | 15 g |
| Avedex W80 dextrin (Deymer Ingredients Ltd) | 50 g |
| Yeast (Allinson) | 3 g |
| Corn Steep Solids (Sigma) | 1 g |
| $KH_2PO_4$ | 2.5 g |
| $K_2HPO_4$ | 2.5 g |
| $(NH_4)_2SO_4$ | 10 g |
| NaCl | 13 g |
| $CaCO_3$ (Caltec) | 10 g |
| $MnCl_2\ 4H_2O$ | 3.5 mg |
| $MgSO_4\ 7H_2O$ | 15 mg |
| $FeSO_4\ 7H_2O$ | 150 mg |
| $ZnSO_4\ 7H_2O$ | 60 mg |
| SAG 471 | 0.1 ml |

Medium was sterilised for 30 min at 121° C.
After sterilisation 15 g of Fructose per L was added.
After 48 h 0.5 g/L of L-lysine was added.
Analytical Methods
Method A Injection volume: 0.005-0.1 mL (as required depending on sensitivity). HPLC was performed on Agilent "Spherisorb" "Rapid Resolution" cartridges SB C8, 3 micron, 30 mm×2.1 mm, running a mobile phase of:
  Mobile phase A: 0.01% Formic acid in pure water
  Mobile phase B: 0.01% Formic acid in Acetonitrile
  Flow rate: 1 mL/minute.

Linear gradient was used, from 5% B at 0 min to 95% B at 2.5 min holding at 95% B until 4 min returning to 5% B until next cycle. Detection was by UV absorbance at 254 nm and/or by mass spectrometry electrospray ionisation (positive or negative) using a Micromass Quattro-Micro instrument.

Method B

Injection volume: 0.02 mL. HPLC was performed on 3 micron BDS C18 Hypersil (ThermoHypersil-Keystone Ltd) column, 150×4.6 mm, maintained at 50° C., running a mobile phase of:

Mobile phase A: Acetonitrile (100 mL), trifluoroacetic acid (1 mL), 1 M ammonium acetate (10 mL) made up to 1 L with deionised water.

Mobile phase B: Deionised water (100 mL), trifluoroacetic acid (1 mL), 1M ammonium acetate (10 mL) made up to 1 L with acetonitrile.

Flow rate 1 mL/minute.

A linear gradient from 55% B-95% B was used over 10 minutes, followed by 2 minutes at 95% B, 0.5 minutes to 55% B and a further 2.5 minutes at 55% B. Compound detection was by UV absorbance at 280 nm.

Method C

The HPLC system comprised an Agilent HP1100 and was performed on 3 micron BDS C18 Hypersil (ThermoHypersil-Keystone Ltd) column, 150×4.6 mm, maintained at 40° C., running a mobile phase of:

Mobile phase A: deionised water.

Mobile phase B: acetonitrile.

Flow rate 1 mL/minute.

The system was coupled to a Bruker Daltonics Esquire3000 electrospray mass spectrometer.

Positive negative switching was used over a scan range of 500 to 1000 Dalton.

A linear gradient from 55% B-95% B was used over 10 minutes, followed by 2 minutes at 95% B, 0.5 minutes to 55% B and a further 2.5 minutes at 55%

Synthetic Methods

All reactions were carried out under anhydrous conditions unless stated otherwise using commercially available dried solvents. Reactions were monitored by LC-UV-MS, on an Agilent 1100 HPLC coupled to a Bruker Daltonics Esquire3000+ mass spectrometer equipped with an electrospray source. Separation was achieved over a Phenomenex Hyperclone column, BDS $C_{18}$ 3u (150×4.6 mm) at 1 mL/min, with a linear gradient of water:acetonitrile v:v 30:70 to 100% acetonitrile over 10 min followed by an isocratic period of 5 min at 100% acetonitrile.

NMR spectra were recorded in $CDCl_3$ and $\delta_H$ and $\delta_C$ chemical shifts are referenced to the solvent (7.26 ppm and 77.0 ppm respectively). Since 39-desmethoxyrapamycin and its derivatives exist as a mixture of conformers all assignments correspond to the major conformer only.

In Vitro Bioassay for Anticancer Activity

In vitro evaluation of compounds for anticancer activity in a panel of 12 human tumour cell lines in a monolayer proliferation assay was carried out at the Oncotest Testing Facility, Institute for Experimental Oncology, Oncotest GmbH, Freiburg. The characteristics of the 12 selected cell lines is summarised in Table 1.

TABLE 1

| Test cell lines | | |
|---|---|---|
| # | Cell line | Characteristics |
| 1 | MCF-7 | Breast, NCI standard |
| 2 | MDA-MB-231 | Breast - PTEN positive, resistant to 17-AAG |
| 3 | MDA-MB-468 | Breast - PTEN negative, resistant to 17-AAG |
| 4 | NCI-H460 | Lung, NCI standard |

TABLE 1-continued

| Test cell lines | | |
|---|---|---|
| # | Cell line | Characteristics |
| 5 | SF-268 | CNS, NCI standard |
| 6 | OVCAR-3 | Ovarian - p85 mutated. AKT amplified. |
| 7 | A498 | Renal, high MDR expression, |
| 8 | GXF 251L | Gastric |
| 9 | MEXF 394NL | Melanoma |
| 10 | UXF 1138L | Uterus |
| 11 | LNCAP | Prostate - PTEN negative |
| 12 | DU145 | Prostate - PTEN positive |

The Oncotest cell lines were established from human tumor xenografts as described by Roth et al. 1999. The origin of the donor xenografts was described by Fiebig et al. 1999. Other cell lines were either obtained from the NCl (H460, SF-268, OVCAR-3, DU145, MDA-MB-231, MDA-MB-468) or purchased from DSMZ, Braunschweig, Germany (LNCAP).

All cell lines, unless otherwise specified, are grown at 37° C. in a humidified atmosphere (95% air, 5% $CO_2$) in a 'ready-mix' medium containing RPMI 1640 medium, 10% fetal calf serum, and 0.1 mg/mL gentamicin (PAA, Cälbe, Germany). Monolayer Assay—Brief Description of Protocol 1:

A modified propidium iodide assay was used to assess the effects of the test compound(s) on the growth of twelve human tumor cell lines (Dengler et al., (1995)).

Briefly, cells were harvested from exponential phase cultures by trypsinization, counted and plated in 96 well flat-bottomed microtitre plates at a cell density dependent on the cell line (5-10,000 viable cells/well). After 24 h recovery to allow the cells to resume exponential growth, 0.01 mL of culture medium (6 control wells per plate) or culture medium containing macbecin are added to the wells. Each concentration is plated in triplicate. Compounds are applied in two concentrations (0.001 µM and 0.01 µM). Following 4 days of continuous exposure, cell culture medium with or without test compound is replaced by 0.2 mL of an aqueous propidium iodide (PI) solution (7 mg/L). To measure the proportion of living cells, cells are permeabilized by freezing the plates. After thawing the plates, fluorescence is measured using the Cytofluor 4000 microplate reader (excitation 530 nm, emission 620 nm), giving a direct relationship to the total number of viable cells.

Growth inhibition is expressed as treated/control×100 (% T/C). For active compounds, $IC_{50}$ & $IC_{70}$ values were estimated by plotting compound concentration versus cell viability.

Example 1

Fermentation and Isolation of 39-desmethoxyrapamycin 39-desmethoxyrapamycin was produced by growing cultures of *S. hygroscopicus* MG2-10 [IJMNOQLhis] and feeding with cyclohexanecarboxylic acid (CHCA) as described below.

Liquid Culture

A vegetative culture of *S. hygroscopicus* MG2-10 [IJM-NOQLhis] was cultivated as described in Materials & Methods. Production cultures were inoculated with vegetative culture at 0.5 mL into 7 mL medium 3 in 50 mL tubes. Cultivation was carried out for 7 days, 26° C., 300 rpm. One millilitre samples were extracted 1:1 acetonitrile with shaking for 30 min, centrifuged 10 min, 13,000 rpm and analysed and quantified according to analysis Method B (see Materials & Methods). Confirmation of product was determined by mass spectrometry using analysis Method C (see Materials & Methods).

The observed rapamycin analogue was proposed to be the desired 39-desmethoxyrapamycin on the basis of the analytical data discussed under characterisation below.

Fermentation

A primary vegetative culture in Medium 4 of *S. hygroscopicus* MG2-10 [IJMNOQLhis] was cultivated essentially as described in Materials & Methods. A secondary vegetative culture in Medium 4 was inoculated at 10% v/v, 28° C., 250 rpm, for 24 h. Vegetative cultures were inoculated at 5% v/v into medium 5 (see Materials & Methods) in a 20 L fermenter. Cultivation was carried out for 6 days at 26° C., 0.5 vvm.≧30% dissolved oxygen was maintained by altering the impeller tip speed, minimum tip speed of 1.18 $ms^{-1}$ maximum tip speed of 2.75 $ms^{-1}$. The feeding of cyclohexanecarboxylic acid was carried out at 24 and 48 hours after inoculation to give a final concentration of 2 mM.

Extraction and Purification

The fermentation broth (30 L) was stirred with an equal volume of methanol for 2 hours and then centrifuged to pellet the cells (10 min, 3500 rpm). The supernatant was stirred with Diaion® HP20 resin (43 g/L) for 1 hour and than filtered. The resin was washed batchwise with acetone to strip off the rapamycin analogue and the solvent was removed in vacuo. The aqueous concentrate was then diluted to 2 L with water and extracted with ethyl acetate (3×2 L). The solvent was removed in vacuo to give a brown oil (20.5 g).

The extract was dissolved in acetone, dried onto silica, applied to a silica column (6×6.5 cm diameter) and eluted with a stepwise gradient of acetone/hexane (20%-40%). The rapamycin analogue-containing fractions were pooled and the solvent removed in vacuo. The residue (2.6 g) was further chromatographed (in three batches) over Sephadex LH20, eluting with 10:10:1 chloroform/heptane/ethanol. The semi-purified rapamycin analogue (1.7 g) was purified by reverse phase (C18) preparative HPLC using a Gilson HPLC, eluting a Phenomenex 21.2×250 mm Luna 5 μm C18 BDS column with 21 mL/min of 65% acetonitrile/water. The most pure fractions (identified by analytical HPLC, Method B) were combined and the solvent removed in vacuo to give 39-desmethoxyrapamycin (563 mg).

Characterisation

The $^1$H NMR spectrum of 39-desmethoxyrapamycin was equivalent to that of a standard (P. Lowden, Ph.D. Dissertation, University of Cambridge, 1997). $^{13}$C-NMR (125 MHz), $\delta_C$ (ppm): 215.75, 208.27, 169.19, 166.71, 140.13, 135.94, 133.61, 130.10, 129.62, 126.80, 126.33, 98.42, 84.77, 84.37, 75.85, 70.91, 67.10, 59.44, 55.82, 51.21, 46.50, 44.17, 41.39, 40.70, 40.16, 38.74, 38.37, 35.44, 35.26, 35.08, 33.78, 33.64, 33.04, 32.37, 31.22, 30.41, 27.24, 27.02, 25.27, 21.48, 20.58, 16.24, 15.95, 15.78, 13.74, 13.00, 10.12.

Figure 2:
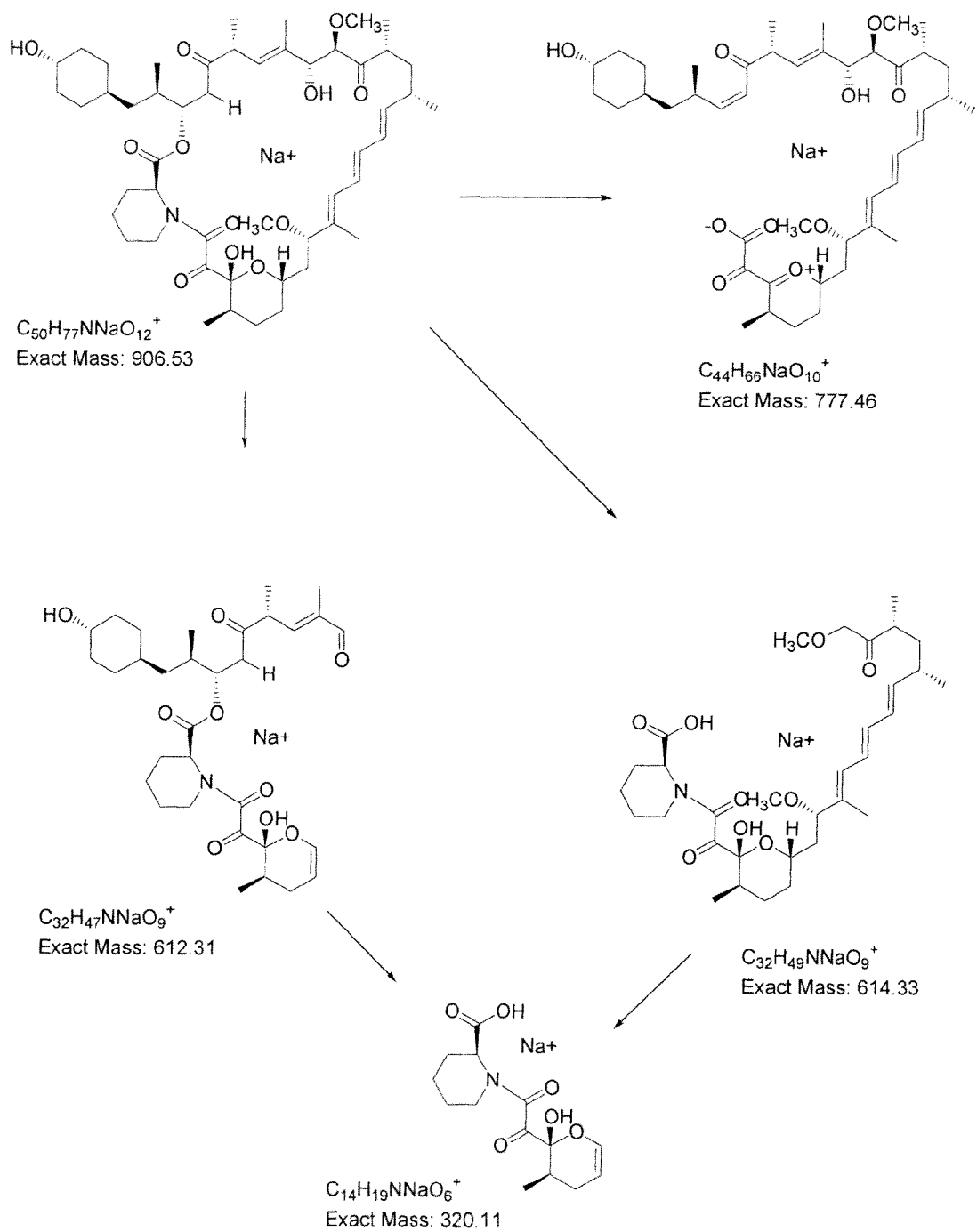
FIG. 2: shows the fragmentation pathway for 39-desmethoxyrapamycin

LCMS and LCMS$^n$ analysis of culture extracts showed that the m/z ratio for the novel rapamycin analogue is 30 atomic mass units lower than that for rapamycin, consistent with the absence of a methoxy group. Ions observed: [M-H]$^-$ 882.3, [M+NH$_4$]$^+$ 901.4, [M+Na]$^+$ 906.2, [M+K]$^+$ 922.2. Fragmentation of the sodium adduct gave the predicted ions for 39-desmethoxyrapamycin following a previously identified fragmentation pathway (FIG. 2) (J. A. Reather, Ph.D. Dissertation, University of Cambridge, 2000). This mass spectrometry fragmentation data narrows the region of the novel rapamycin analogue where the loss of a methoxy has occurred to the fragment C28-C42 that contains the cyclohexyl moiety. This mass spectrometry fragmentation data is entirely consistent with 39-desmethoxyrapamycin.

Example 2

39-desmethoxy-40-O-[2,2-bis(hydroxymethyl)propionyl]rapamycin

39-Desmethoxy-40-O-[2,2-bis(hydroxymethyl)propionyl]rapamycin was synthesised from 39-desmethoxyrapamycin according to the following procedure.

2.1 Synthesis of 39-desmethoxy-28-O-trimethylsilyl rapamycin

39-Desmethoxyrapamycin (170 mg, 0.17 mmol) and imidazole (51 mg, 0.75 mmol) were dissolved in 5 mL ethyl acetate at 0° C. To this cold solution chlorotrimethylsilane (77 mg, 0.09 mL, 0.71 mmol) was added drop wise over a period of 10 min. Stirring was continued for additional 60 min to complete the formation of the 28,39-bis-O-trimethylsilyl ether. After that period 0.4 mL aqueous 0.5 N sulfuric acid was added and the mixture was stirred for 2.5 h at 0° C. 20 mL ethyl acetate was added and the organic layer was washed with brine, saturated sodium hydrogen carbonate solution and water. Drying over sodium sulfate and concentration under reduced pressure yielded the 28-O-trimethylsilyl ether as a colourless solid which was used without further purification for the subsequent reaction.

$^1$H-NMR (400 MHz, CDCl$_3$), δ (ppm): 4.07 (d, 1H, J=6.5 Hz, C(28)-H), 0.00 (s, 9H, 28-O-TMS).

MS (ESI) m/z 978 [M+Na]$^+$.

2.2. Synthesis of 2,4,6-trichlorobenzoic 2',2',5'-trimethyl-1',3'-dioxane-5' carboxylic anhydride 2,2-Dimethoxypropane (13.5 g, 130 mmol) and p-toluenesulfonic acid monohydrate (100 mg, 0.53 mmol, 0.4 mol %) were added to a solution of 2,2-bis(hydroxymethyl)propionic acid (13.5 g, 100 mmol) in acetone (100 mL). The reaction mixture was stirred at room temperature for 2 h. After that period moist sodium hydrogencarbonate was added and the mixture was stirred for further 5 minutes. The supernatant was decanted off and concentrated under reduced pressure. The resulting solid was treated with diethyl ether (3×50 mL) and the combined organic extracts were concentrated under reduced pressure to yield a white solid, 16.2 g (93%)

$^1$H-NMR (400 MHz, CDCl$_3$), δ (ppm): 4.19 (d, 1H, J=12.0 Hz) 3.68 (d, 1H, J=12.0 Hz) 1.45 (s, 1H) 1.41 (s, 1H) 1.20 (s, 1H).

This material was then converted into an activated mixed anhydride by the method of U.S. Pat. No. 5,362,718. Thus, the acetonide (1.04 g, 5.98 mmol) was dissolved in THF (20 mL) cooled to 0° C. and treated with the dropwise addition of triethylamine (0.83 mL, 5.98 mmol) and 2,4,6-trichlorobenzoyl chloride (0.93 mL, 5.98 mmol). The reaction was then stirred at room temperature for 5 hours. The resulting precipitate was filtered and washed with THF (10 mL). The combined filterate was reduced in vacuo to a white amorphous solid which was used (as below) without further purification.

2.3. Synthesis of 39-desmethoxyrapamycin 28-O-trimethylsilyl ether, 40-ester with 2,2,5-trimethyl[1.3-dioxane]-5-carboxylic acid Crude 28-O-trimethylsilyl-39-desmethoxyrapamycin (200 mg, from 0.17 mmol 39-desmethoxyrapamycin) from example 2.1 was dissolved in 2 mL dichloromethane. The solution was cooled to 0° C. and DMAP (102 mg, 0.84 mmol) was added. Then, a solution of 2,4,6-trichlorobenzoic 2',2',5'-trimethyl-1',3'-dioxane-5' carboxylic anhydride (159 mg, 0.42 mmol) in 1 mL dichloromethane was added over a period of 10 min. The reaction mixture was stirred at 0° C. for 5 h and the conversion was monitored by LC/MS. The reaction mixture was diluted with 7 mL of dichloromethane and quenched by addition of 5 mL water. The organic layer was separated and washed successively with 0.5 N sulfuric acid, sodium hydrogencarbonate solution and water. Drying over sodium sulfate and concentration under reduced pressure gave the title compound as colourless foam, which was used immediately without further purification. MS (ESI) m/z 1111 [M-H]$^-$
2.4. 39-desmethoxy-40-O-[2,2-bis(hydroxymethyl)propionyl]rapamycin Crude 39-desmethoxyrapamycin-28-O-trimethylsilyl ether 40-ester with 2,2,5-trimethyl[1.3-dioxane]-5-carboxylic acid from example 2.3 was dissolved in 2 mL acetone and 0.5 mL of 0.5 N sulfuric acid was added. The reaction mixture was stirred for 5 h at room temperature and subsequently neutralised by the addition of 5 mL saturated sodium hydrogencarbonate solution and 5 mL water. The aqueous mixture was extracted with ethyl acetate and the combined organic extracts were dried over sodium sulphate. Concentration under reduced pressure gave a colourless solid which was purified by size exclusion chromatography on Sephadex LH20 using chloroform/heptane/ethanol (v:v:v 10:10:1) as eluents.

$^1$H-NMR (500 MHz, CDCl$_3$), δ (ppm): 4.72 (m, 1H, C(40)-H), 3.87 (m, 2H), 3.69 (m, 2H), 1.03 (s, 3H); $^{13}$C-NMR (125 MHz, CDCl$_3$), δ (ppm): 175.52, 74.04 (C(40)), 68.73 (2C), 48.90, 17.09.

MS (ESI) m/z 1023 [M+Na]$^+$.

Example 3

39-desmethoxy-40-O-(2-hydroxy)ethyl rapamycin 3.1. 2-(tert-butyldimethylsilyl)oxyethyl triflate A solution of 2-(tert-butyldimethylsilyl)-ethylene glycol (125 mg, 0.71 mmol) and 2,6-lutidene (0.08 mL, 0.69 mmol) in 6 ml dichloromethane was cooled to −78° C. Trifluoromethanesulfonic anhydride (0.11 mL, 0.65 mmol) was added over a period of 5 min and stirring was continued for additional 15 min at −78° C. to complete the formation of the triflate. The triflate was used in situ for the reaction as described in 3.2 below.

3.2. 40-O-[2-(tert-butyldimethylsilyl)]ethyl-39-desmethoxyrapamycin

39-Desmethoxyrapamycin (300 mg, 0.34 mmol) and 2,6-di-tert-butylpyridine (1.5 mL, 6.68 mmol) were treated with 2-(tent-butyldimethylsilyl)oxyethyl triflate (0.65 mmol in 6 mL dichloromethane) at room temperature. This solution was concentrated to a third of its original volume with a gentle stream of nitrogen and the resulting suspension was stirred for further 72 h at room temperature. After that period saturated sodium hydrogencarbonate solution (5 mL) and water (5 mL) were added and the mixture was stirred for 30 min. The organic layer was separated and the aqueous phase was extracted with ethyl acetate (2×5 mL). The combined organic extracts were dried over sodium sulfate and concentrated under reduced pressure to give a colourless oil. Purification by column chromatography on silica using a gradient from hexane to hexane/acetone (v:v 1:1) gave the product as a colourless solid.

$^1$H-NMR (500 MHz, CDCl$_3$), δ (ppm): 4.16 (d, 1H, J=6.5 Hz, C(28)-H), 3.73 (t, 2H, J=5.7 Hz), 3.52 (t, 2H, J=57 Hz), 0.89 (s, 9H), 0.06 (s, 6H); $^{13}$C-NMR (125 MHz, CDCl$_3$), δ (ppm): 76.61 (C-40), 69.31 (CH$_2$), 63.03 (CH$_2$), 25.92 (3C), 18.36, −5.23 (2C).

MS (ESI) m/z 1065 [M+Na]$^+$ 3.3. 39-Desmethoxy-40-O-(2-hydroxy)ethyl rapamycin

A solution of 40-O-[2-(tert-butyldimethylsilyl)]ethyl-39-desmethoxy rapamycin (160 mg, 0.15 mmol) in 2 mL acetone was treated with 0.3 mL of 0.5 N sulfuric acid at room temperature. The solution was allowed to stand at room temperature for 3 h and was subsequently quenched by the addition of 5 mL saturated sodium hydrogencarbonate solution and 10 mL water. The aqueous mixture was extracted with ethyl acetate (3×10 mL) and the combined organic extracts were dried over sodium sulfate. Concentration under reduced pressure gave a colourless solid which was further purified by HPLC (water/acetonitrile v:v 20/80).

$^1$H-NMR (500 MHz, CDCl$_3$), δ (ppm): 4.16 (d, 1H, J=6 Hz), 3.70 (m, 2H), 3.57 (m, 2H), 3.20 (m, 1H, C(40)-H); $^{13}$C-NMR (125 MHz, CDCl$_3$), δ (ppm): 78.65 (C-40), 77.20 (C-28), 68.93 (CH$_2$O), 62.10 (CH$_2$O).

MS (ESI) m/z 951 [M+Na]$^+$.

Example 4

39-desmethoxy-40-O-[2,2-bis(hydroxymethyl)propionyl]rapamycin through lipase catalysed esterification of 39-desmethoxyrapamycin A mixture of 39-desmethoxyrapamycin (720 mg, 0.82 mmol), vinyl 2,2,5-trimethyl[1.3-dioxane]-5-carboxylate (244 mg, 1.22 mmol), lipase PS-C "Amano" II (720 mg) and molecular sieves 0.5 nm (250 mg) in anhydrous tert-Butyl methyl ether (3.5 mL) was heated to 43° C. under an atmosphere of argon. After 48 h LC/MS monitoring showed complete conversion of the starting material. THF (10 mL) was added and the mixture was filtered through a pad of celite. The enzyme was washed with THF (2×10 mL) and the combined organic extracts were concentrated under reduced pressure. The residue was dissolved in THF (50 mL) and H$_2$SO$_4$ (15 mL, 0.5 N) was added. The solution was allowed to stand at room temperature for 5 h and the reaction was subsequently quenched by the addition of NaHCO$_3$ (50 mL, 5%) and brine (50 mL). The aqueous mixture was extracted with EtOAc (3×100 mL) and the combined organic extracts were dried over MgSO$_4$. Removal of solvents gave the product as semi-solid. Purification by flash chromatography (hexane/acetone 1:1) gave the product as a colourless solid.

The NMR data are identical with that of example 2.4

Figure 3:
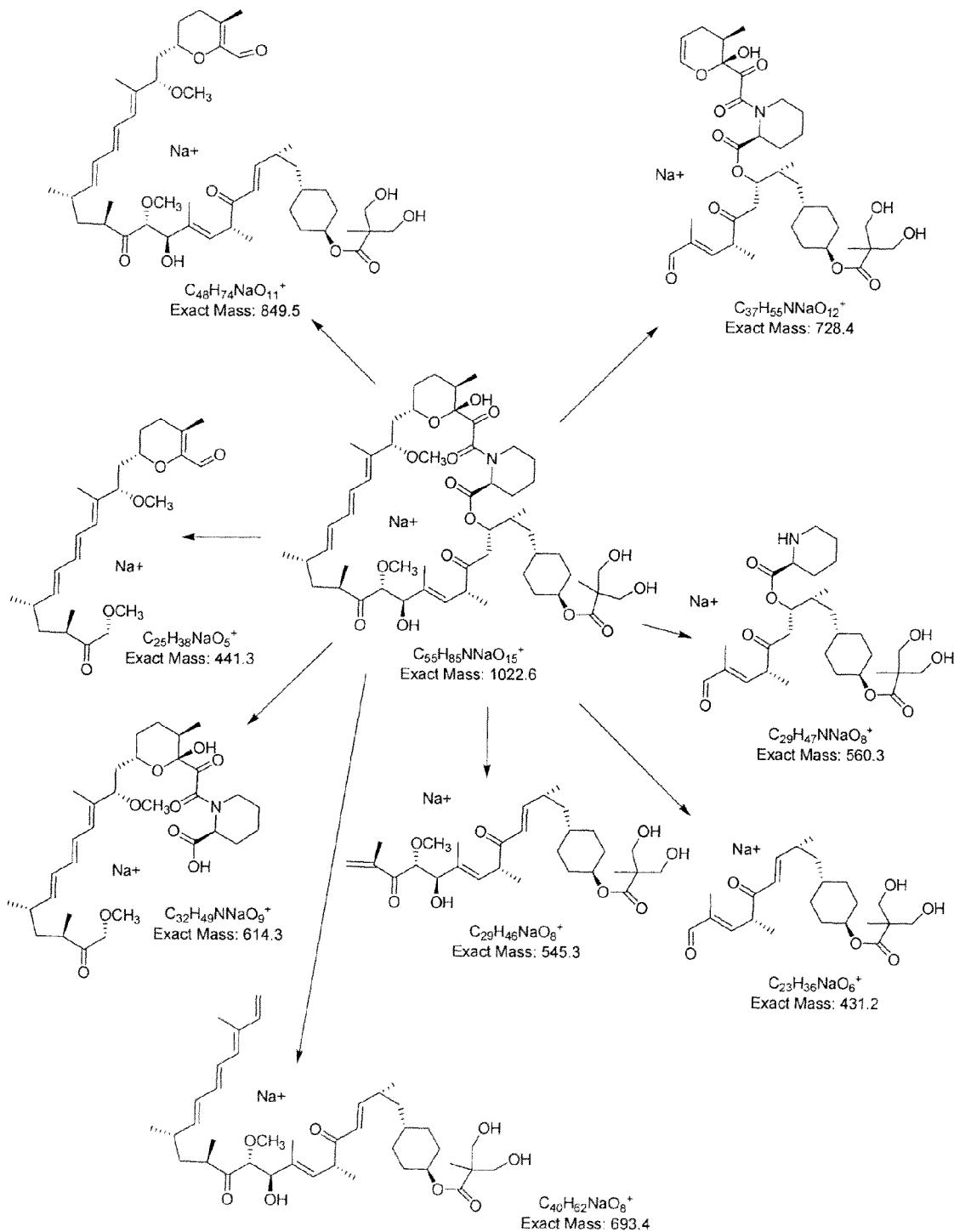
FIG. 3: shows the fragmentation pathway for 39-desmethoxy-40-O-[2,2-bis(hydroxymethyl)propionyl]rapamycin.

MS (ESI) m/z 1022 [M+Na]$^+$ Fragmentation of the sodium adduct gave ions at m/z 850, 728, 693, 614, 560, 545, 441 and 431 in accordance with the fragmentation pattern shown in FIG. 3.

Example 5

39-Desmethoxy-40-O-[2-hydroxyethyl 3-hydroxy-2-(hydroxymethyl)-2-methylpropanoate]rapamycin A mixture of 39-Desmethoxy-40-O-(2-hydroxy)ethyl rapamycin (40 mg, 0.04 mmol), vinyl 2,2,5-trimethyl[1.3-dioxane]-5-carboxylate (25 mg, 0.13 mmol), lipase PS-C "Amano" II (40 mg) and molecular sieve 0.5 nm (40 mg) in anhydrous tert-Butyl methyl ether (2 mL) was heated to 43° C. under an atmosphere of argon. After 72 h LC/MS monitoring showed complete conversion of the starting material. THF (10 mL) was added and the mixture was filtered through a pad of celite. The enzyme was washed with THF (2×10 mL) and the combined organic extracts were concentrated under reduced pressure. The residue was dissolved in acetone (7.5 mL) and H$_2$SO$_4$ (2.5 ml, 0.5 N) were added. The solution was allowed to stand at room temperature for 2 h and the reaction subsequently quenched by the addition of sat. NaHCO$_3$ (10 mL) and water (10 mL). The aqueous mixture was extracted with EtOAc (3×10 ml) and the combined organic extracts were dried over MgSO$_4$. Removal of solvents gave the product as yellowish solid. Purification by preparative HPLC on a Phenomenex 21.2×50 mm Luna 5 μm C18 BDS column using a gradient from 70:30 MeCN/water to 100% MeCN over 15 min gave the product as a colourless solid.

Figure 4:
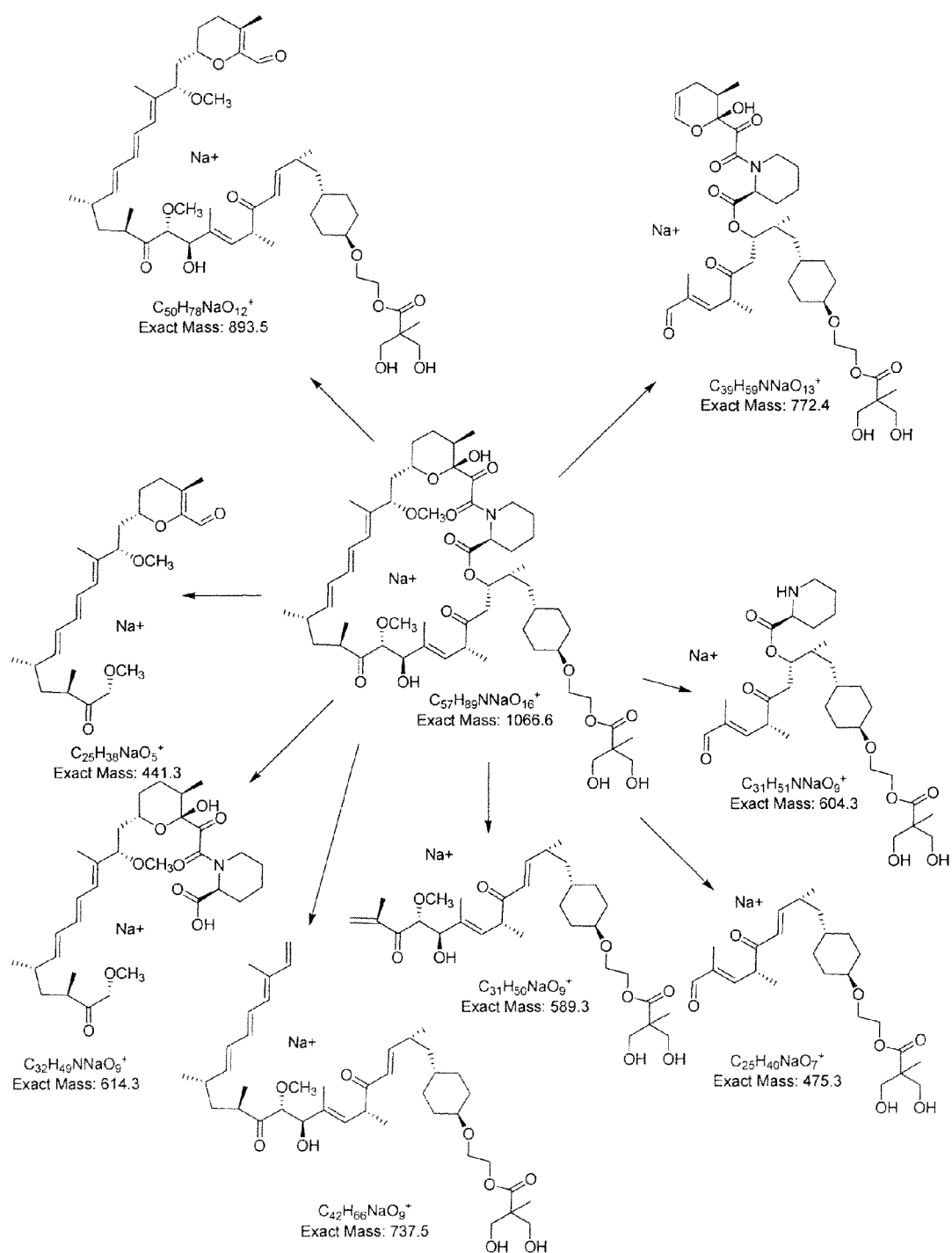
FIG. 4: shows the fragmentation pathway for 39-desmethoxy-40-O-[2-hydroxyethyl 3-hydroxy-2-(hydroxymethyl)-2-methylpropanoate]rapamycin

MS (ESI) m/z 1067 [M+Na]$^+$ Fragmentation of the sodium adduct gave ions at m/z 894, 772, 738, 614, 604, 589, 475 and 441 in accordance with the fragmentation pattern shown in FIG. 4.

Example 6

27-O-desmethyl-39-desmethoxy-40-O-[2,2-bis(hydroxymethyl)propionyl]rapamycin 6.1  27-O-desmethyl-39-desmethoxyrapamycin, 40-ester with 2,2,5-trimethyl[1.3-dioxane]-5-carboxylic acid A mixture of 27-O-desmethyl-39-desmethoxy rapamycin (30 mg, 0.034 mmol), vinyl 2,2,5-trimethyl[1.3-dioxane]-5-carboxylate (34 mg, 0.17 mmol), lipase PS-C "Amano" II (30 mg) and molecular sieve 0.5 nm (30 mg) in anhydrous tert-Butyl methyl ether (2 mL) was heated to 43° C. under an atmosphere of argon for 72 h. THF (10 mL) was added and the mixture was filtered through a pad of celite. The enzyme was washed with THF (2×10 mL) and the combined organic extracts were concentrated under reduced pressure to give a yellowish semi-solid. Purification by flash chromatography using hexane:acetone (v:v 2:1) gave the product as a pale yellow solid.

MS (ESI) m/z 1049 [M+Na]$^+$ 6.2  27-O-desmethyl-39-desmethoxy-40-O-[2,2-bis(hydroxymethyl)propionyl]rapamycin The material from 6.1 was dissolved in acetone (6 mL) and H$_2$SO$_4$ (2 mL, 0.5 N) was added. The solution was allowed to stand at room temperature for 2 h and the reaction subsequently quenched by the addition of sat. NaHCO$_3$ (10 mL) and water (10 mL). The aqueous mixture was extracted with EtOAc (3×10 mL) and the combined organic extracts were dried over MgSO$_4$. Removal of solvents gave the product as yellowish solid. Purification by preparative HPLC on a Phenomenex 21.2×50 mm Luna 5 μm C18 BDS column using a gradient from 70:30 MeCN/water to 100% MeCN over 15 min gave the product as a colourless solid.

Figure 5:
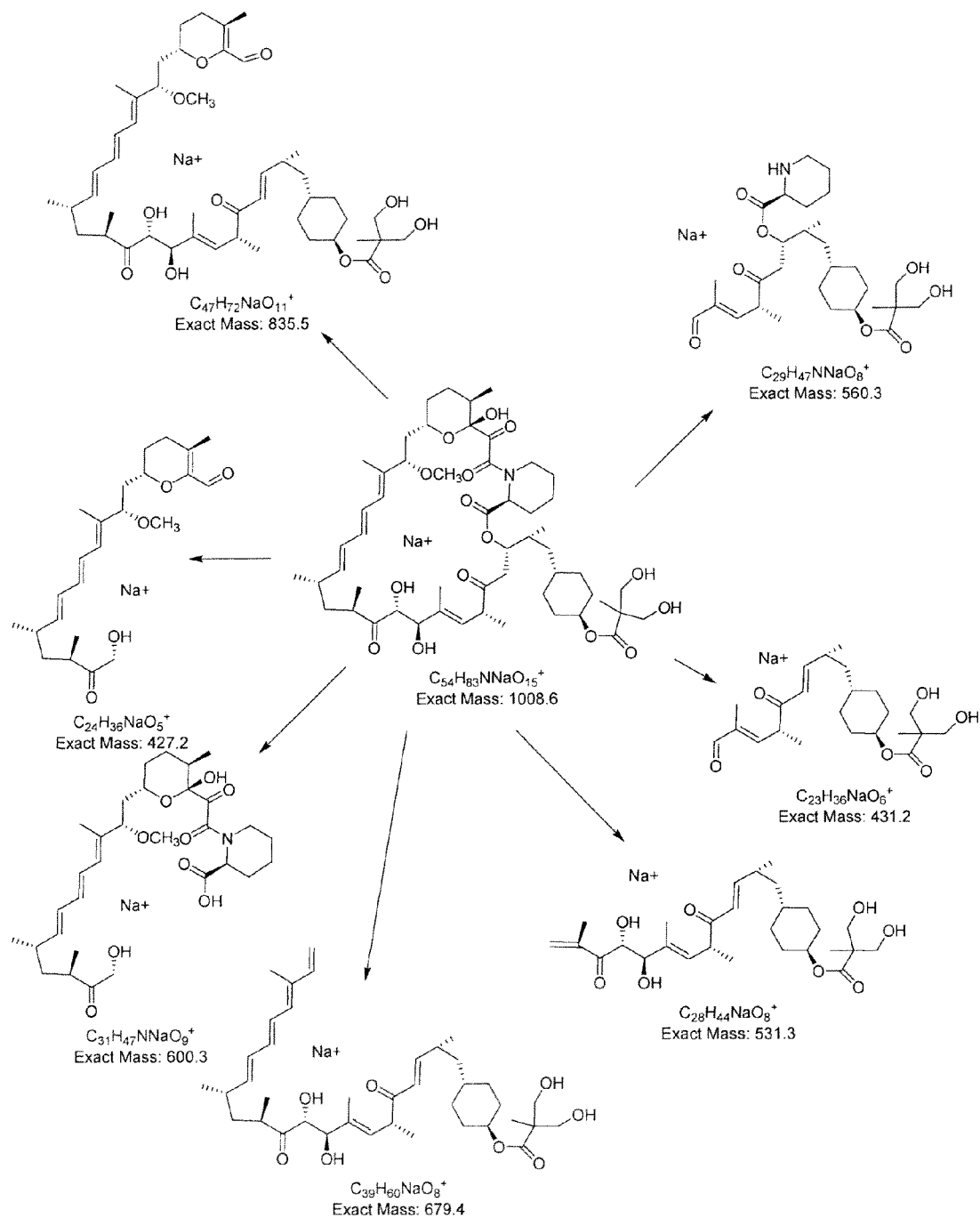
FIG. 5: shows the fragmentation pathway for 27-O-desmethyl-39-desmethoxy-40-O-[2,2-bis(hydroxymethyl)propionyl]rapamycin

MS (ESI) m/z 1009 [M+Na]$^+$ Fragmentation of the sodium adduct gave ions at m/z 836, 679, 600, 560, 531, 431, 427 in accordance with the fragmentation pattern shown in FIG. 5 1H NMR (500 MHz, CDCl$_3$) δ ppm 4.73 (m, 1H, C(40)-H), 4.32 (d, J=4.5 Hz, 1H, C(27)-H), 4.19 (d, J=4.5 Hz, 1H, C(28)-H), 3.89 (m, 2H), 3.70 (m, 2H) 1.03 (s, 3H).

Example 7

In vitro evaluation of anticancer activity of 39-desmethoxy-40-O-(2-hydroxy)ethyl rapamycin and 39-desmethoxy-40-O-[2,2-bis(hydroxymethyl)propionyl]rapamycin In vitro evaluation of 39-desmethoxy-40-O-(2-hydroxy) ethyl rapamycin and 39-desmethoxy-40-O-[2,2-bis(hydroxymethyl)propionyl]rapamycin for anticancer activity in a panel of 12 human tumour cell lines in a monolayer proliferation assay was carried out as described as Protocol 1 in the general methods above using a modified propidium iodide assay.

The results are displayed in Table 3 below; each result represents the mean of duplicate experiments. Table 4 shows the mean IC$_{50}$ and IC$_{70}$ for the compounds across the cell lines tested, with rapamycin shown as a reference.

TABLE 3

| | Cell Growth (Test/Control (%) at drug concentration) | | | | | |
|---|---|---|---|---|---|---|
| | Rapamycin | | 39-desmethoxy-40-O-(2-hydroxy)ethyl rapamycin | | 39-desmethoxy-40-O-[2,2-bis(hydroxymethyl)propionyl]-rapamycin | |
| Cell line | 1 μM | 10 μM | 1 μM | 10 μM | 1 μM | 10 μM |
| SF268 | 53.5 | 46 | 63 | 7 | 62.5 | 12 |
| 251L | 75.5 | 40 | 90 | 31 | 85.5 | 13 |
| H460 | 67 | 66 | 76 | 25 | 66 | 12 |
| MCF7 | 68.5 | 26.5 | 77 | 10 | 67 | 9 |
| MDA231 | 67 | 63.5 | | | 70.5 | 13.5 |
| MDA468 | 56.5 | 32 | | | 66 | 9 |
| 394NL | 45 | 44 | 55 | 6 | 46 | 13 |
| OVCAR3 | 69 | 69.5 | 85 | 9 | 73.5 | 39 |
| DU145 | 50.5 | 54 | 56 | 7 | 62.5 | 13.5 |
| LNCAP | 61 | 34 | 49 | 18 | 48.5 | 20.5 |
| A498 | 58.5 | 48.5 | | | 66 | 19.5 |
| 1138L | 42 | 21.5 | 59 | 4 | 50 | 7.5 |

TABLE 4

| | Rapamycin | 39-desmethoxy-40-O-(2-hydroxy)ethyl rapamycin | 39-desmethoxy-40-O-[2,2-bis(hydroxymethyl)propionyl]rapamycin |
|---|---|---|---|
| Mean IC$_{50}$ (microM) | 3.5 | 2.2* | 2.0 |
| Mean IC$_{70}$ (microM) | 9.1 | 5.513* | 4.5 |

*mean was based on the 9 cell lines for which data was available

Example 8

In Vitro Binding Assays

FKBP12

FKBP12 reversibly unfolds in the chemical denaturant guandinium hydrochloride (GdnHCl) and the unfolding can be monitored by the change in the intrinsic fluorescence of the protein (Main et al, 1998). Ligands which specifically bind and stabilise the native state of FKBP12 shift the denaturation curve such that the protein unfolds at higher concentrations of chemical denaturant (Main et al, 1999). From the difference in stability, the ligand-binding constant can be determined using equation 1.

$$\Delta G_{app} = \Delta G_{D-N}^{H_2O} + RT\ln\left(1 + \frac{[L]}{K_d}\right) \quad (1)$$

where $\Delta G_{app}$ is the apparent difference in free energy of unfolding between free and ligand-bound forms, $\Delta G_{D-N}^{H_2O}$ is the free energy of unfolding in water of free protein, [L] the concentration of ligand and $K_d$ the dissociation constant for the protein-ligand complex (Meiering et al, 1992). The free energy of unfolding can be related to the midpoint of the unfolding transition using the following equation:

$$\Delta G_{D-N}^{H_2O} = m_{D-N}[D]_{50\%} \quad (2)$$

where $m_{D-N}$ is a constant for a given protein and given denaturant and which is proportional to the change in degree of exposure of residues on unfolding (Tanford 1968 and Tanford 1970), and $[D]_{50\%}$ is the concentration of denaturant corresponding to the midpoint of unfolding. We defined $\Delta\Delta G_{D-N}^L$, the difference in the stability of FKBP12 with rapamycin and unknown ligand (at the same ligand concentration), as:

$$\Delta\Delta G_{D-N}^L = <m_{D-N}>\Delta[D]_{50\%} \quad (3)$$

where $<m_{D-N}>$ is the average m-value of the unfolding transition and $\Delta[D]_{50\%}$ the difference in midpoints for the rapamycin-FKBP12 unfolding transition and unknown-ligand-FKBP12 complex unfolding transition. Under conditions where $[L]>K_d$, then, $\Delta\Delta G_{D-N}$, can be related to the relative $K_d$s of the two compounds through equation 4:

$$\Delta\Delta G_{D-N}^L = RT\ln\frac{K_d^X}{K_d^{rap}} \quad (4)$$

where $K_d^{rap}$ is the dissociation constant for rapamycin and $K_d^X$ is the dissociation constant for unknown ligand X. Therefore, $$K_d^X = K_d^{rap}\exp\left(\frac{<m_{D-N}>\Delta[D]_{50\%}}{RT}\right) \quad (5)$$

Fitting each denaturation curve generates values for $m_{D-N}$ and $[D]_{50\%}$, which can be used to calculate an average m-value, $<m_{D-N}>$, and $\Delta[D]_{50\%}$, and hence $K_d^X$. The literature value of $K_d^{rap}$ of 0.2 nM is used.

In some cases, due to the low solubility of the test compound, lower concentrations of the test compound were used than in the rapamycin control experiment. In these cases, the differences between the test compound concentration and the rapamycin control concentration were taken into account using equation 6 below:

$$K_d^X = K_d^{rap}\frac{(1+[L]_x)}{(1+[L]_{rap})}\exp\left(\frac{<m_{D-N}>\Delta[D]_{50\%}}{RT}\right) \quad (6)$$

TABLE 5

FKBP-12 in vitro binding assay results

| | Ligand [L] μM | FKBP12 $K_d$ (nM) |
|---|---|---|
| Rapamycin | 10 | 0.2 |
| 39-desmethoxy-40-O-(2-hydroxy)ethyl rapamycin | 1.6 | 3.7 |
| 39-desmethoxy-40-O-[2,2-bis(hydroxymethyl)propionyl]rapamycin | 6.67 | 1.1 | mTOR

Inhibition of mTOR was established indirectly via the measurement of the level of phosphorylation of the surrogate markers of the mTOR pathway and p70S6 kinase and S6 (Brunn et al., 1997; Mothe-Satney et al., 2000; Tee and Proud, 2002; Huang and Houghton, 2002).

Figure 6:
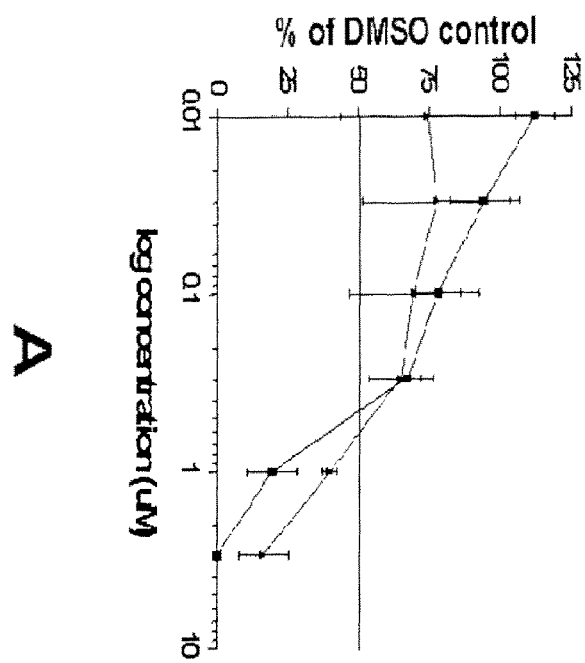
FIG. 6: shows the mTOR inhibitory activity of 39-desmethoxy-40-O-[2,2-bis(hydroxymethyl)propionyl]rapamycin (A—filled triangles) and 39-desmethoxy-40-O-(2-hydroxy)ethyl rapamycin (B—filled triangles) compared to rapamycin (filled squares).
Figure 6:
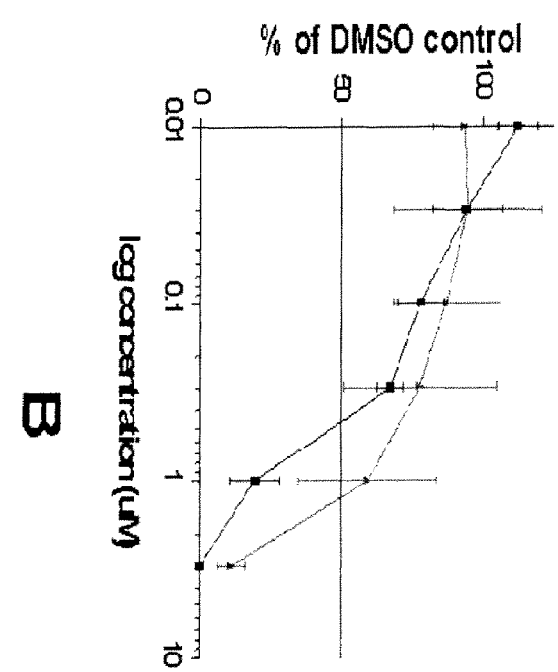

HEK293 cells were co-transfected with FLAG-tagged mTOR and myc-tagged Raptor, cultured for 24 h then serum starved overnight. Cells were stimulated with 100 nM insulin then harvested and lysed by 3 freeze/thaw cycles. Lysates were pooled and equal amounts were immunoprecipitated with FLAG antibody for the mTOR/Raptor complex. Immunoprecipitates were processed: samples treated with compound (0.00001 to 0.003 mM) were pre-incubated for 30 min at 30° C. with FKBP12/rapamycin. FKBP12/39-desmethoxyrapamycin derivative or vehicle (DMSO), non-treated samples were incubated in kinase buffer. Immunoprecipitates were then subject to in vitro kinase assay in the presence of 3 mM ATP, 10 mM $Mn^{2+}$ and GST-4E-BP1 as substrate. Reactions were stopped with 4× sample buffer then subject to 15% SDS-PAGE, wet transferred to PVDF membrane then probed for phospho-4E-BP1 (T37/46). Western blot bands were quantitated by image analysis using Image J (http://rsb.info.nih.gov/ij/). FIG. 6A shows dose-response curves for rapamycin (filled squares) and 39-desmethoxy-40-O-[2,2-bis(hydroxymethyl)propionyl]rapamycin (filled triangles). FIG. 6B shows dose-response curves for rapamycin (filled squares) and 39-desmethoxy-40-O-(2-hydroxy)ethyl rapamycin (filled triangles).

Alternatively. HEK293 cells were seeded into 6 well plates and pre-incubated for 24 h and then serum starved overnight. Cells were pre-treated with vehicle or compound for 30 min at 30° C., then stimulated with 100 nM insulin for 30 min at 30° C. and lysed by 3 freeze/thaw cycles and assayed for protein concentration. Equal amounts of protein were loaded and separated on SDS-PAGE gels. The protein was wet transferred to PVDF membrane then probed for phospho-S6 (S235/36) or phospho-p70 S6K (T389). Western blot bands were quantitated by image analysis using Image J (http://rsb.info.nih.gov/ij/).

REFERENCES

Alarcon, C. M., Heitman, J., and Cardenas, M. E. (1999) Protein kinase activity and identification of a toxic effector domain of the target of rapamycin TOR proteins in yeast. *Molecular Biology of the Cell* 10: 2531-2546.

Alvarez, M., Paull, K., Monks, A., Hose, C., Lee, J. S., Weinstein, J., Greyer, M., Bates, S., Fojo, T., 1995. Generation of a drug resistance profile by quantitation of mdr-1/P-glycoprotein in the cell lines of the National Cancer Institute Anticancer Drug Screen. *Journal of Clinical Investigation*, 95, 2205-2214.

Aparicio, J. F., Molnár, I., Schwecke, T., König, A., Haydock, S. F., Khaw, L. E., Staunton, J., and Leadlay, P. F. (1996) Organization of the biosynthetic gene cluster for rapamycin in *Streptomyces hygroscopicus*: analysis of the enzymatic domains in the modular polyketide synthase. *Gene* 169: 9-16.

Baker, H., Sidorowicz, A., Sehgal, S. N., and Vézina, C. (1978) Rapamycin (AY-22,989), a new antifungal antibiotic. III. In vitro and in vivo evaluation, *Journal of Antibiotics* 31: 539-545.

Boulay, A., Zumstein-Mecker, S., Stephan, C., Beuvink, I., Zilbermann, F., Haller, R., Tobler, S., Heusser, C., O'Reilly, T., Stolz, B., Marti, A., Thomas, G., Lane, H. A., 2004, Antitumor efficacy of intermittent treatment schedules with the rapamycin derivative RAD001 correlates with prolonged inactivation of ribosomal protein S6 kinase 1 in peripheral blood mononuclear cells. *Cancer Res.* 64(1), 252-61.

Boyd, M. R. and Paull, K. D., 1995. Some Practical Considerations and Applications of the National Cancer Institute In Vitro Anticancer Drug Discovery Screen. *Drug Development Research* 34, 91-109, Brown, E. J., Albers, M. W., Shin, T. B., Ichikawa, K., Keith, C. T., Lane, W. S., and Schreiber, S. L. (1994) A mammalian protein targeted by G1-arresting rapamycin-receptor complex. *Nature* 369: 756-758.

Brunn, G. J., Fadden, P., Haystead, T. A., Lawrence, J. C. Jr. 1997 The mammalian target of rapamycin phosphorylates sites having a (Ser/Thr)-Pro motif and is activated by antibodies to a region near its COOH terminus. *J Biol. Chem.* 272(51), 32547-32550.

Brunn, G. J., Williams, J., Sabers, C., Wiederrecht, G., Lawrence, J. C., and Abraham, R. T. (1996) Direct inhibition of the signaling functions of the mammalian target of rapamycin by the phosphoinositide 3-kinase inhibitors, wortmannin and LY294002. *EMBO Journal* 15: 5256-5267.

Carlson, R. P., Hartman, D. A., Tomchek, L. A., Walter, T. L., Lugay, J. R., Calhoun, W., Sehgal, S. N., Chang, J. Y. (1993). Rapamycin, a potential disease-modifying antiarthritic drug, J. Pharmacol. Exp. Ther. 266(2):1125-38.

Crowe A, Bruelisauer A, Duerr L, Guntz P. Lemaire M. (1999) Absorption and intestinal metabolism of SDZ-RAD and rapamycin in rats. *Drug Metab Dispos,* 27(5), 627-32

Dengler W. A., Schulte J., Berger D. P., Mertelsmann R. and Fiebig H H. (1995) Development of a propidium iodide fluorescence assay for proliferation and cytotoxicity assay. *Anti-Cancer Drugs,* 6:522-532.

DiLella, A. G., and Craig, R. J. (1991) Exon organization of the human FKBP-12 gene: correlation with structural and functional protein domains. *Biochemistry* 30: 8512-8517.

Dudkin, L. Dilling, M. B., Cheshire, P. J., Harwood, F. C., Hollingshead, M., Arbuck, S. G., Travis, R., Sausville, E. A., Houghton, P. J. (2001). Biochemical correlates of mTOR inhibition by the rapamycin ester CCI-779 and tumor growth inhibition. Clin. Cancer Res. 7(6):1758-64

Evans D. A., Gage J. R. and Leighton J. L. (1992) Assymetric synthesis of calyculin A. 3. Assemblage of the calyculin skeleton and the introduction of a new phosphate monoester synthesis. *J. Org. Chem.,* 57:1964-1966

Fiebig H. H., Dengler W. A. and Roth T. (1999) Human tumor xenografts: Predictivity, characterization, and discovery of new anticancer agents. In: Fiebig H H, Burger A M (eds). Relevance of Tumor Models for Anticancer Drug Development. *Contrib. Oncol.,* 54: 29-50.

Findlay J. A, and Radics, L. (1980) *Canadian Journal of Chemistry* 58:579.

Fishbein, T. M., Florman, S., Gondolesi, G., Schiano, T., LeLeiko, N., Tschernia, A., Kaufman, S. (2002). Intestinal transplantation before and after the introduction of sirolimus. *Transplantation.* 73(10):1538-42.

Foey, A., Green, P., Foxwell, B., Feldmann, M., Brennan, F. (2002). Cytokine-stimulated T cells induce macrophage IL-10 production dependent on phosphatidylinositol 3-kinase and p70S6K: implications for rheumatoid arthritis. *Arthritis Res.* 4(1):64-70. Epub 2001 Oct. 10.

Furniss B. S., Hannaford A. J., Smith P. W. G. and Tatchell A. R. (1989) *Vogel's textbook of practical organic chemistry,* 5th Ed, Pearson, Prentice Hall, Harlow, UK.

Gallant-Haidner H L, Trepanier D J, Freitag D G, Yatscoff R W. 2000, "Pharmacokinetics and metabolism of sirolimus". *Ther Drug Monit.* 22(1), 31-5.

Grass, G. M., Rubas, W., Jezyk, N., (1992) Evaluation of CACO-2 monolayers as a predictor of drug permeability in colonic tissues. *FASEB Journal,* 6, A1002.

Gregory, C. R., Huie, P., Billingham, M. E. and Morris, R. E. (1993). Rapamycin inhibits arterial intimal thickening caused by both alloimmune and mechanical injury. Its effect on cellular, growth factor and cytokine response in injured vessels. *Transplantation* 55(6):1409-1418.

Gregory M A, Gaisser S, Lill R E, Hong H. Sheridan R M, Wilkinson B. Petkovic H. Weston A J, Carletti I, Lee H L, Staunton J, Leadlay P F. (2004) "Isolation and characterization of pre-rapamycin, the first macrocyclic intermediate in the biosynthesis of the immunosuppressant rapamycin by *S. hygroscopicus*". *Angew Chem Int Ed Engl.* 43(19), 2551-3

Gu, J. Ruppen M E, Cai P. (2005), "Lipase-Catalyzed Regioselective Esterification of Rapamycin: Synthesis of Temsirolimus (CCI-779). Org. Lett. 7(18): 3945-3948.

Guba, M., von Breitenbuch, P., Steinbauer, M., Koehl, G., Flegel, S., Hornung, M., Bruns. C J, Zuelke, C., Farkas, S., Anthuber, M., Jauch, K. W., and Geissler, E. K. (2002) Rapamycin inhibits primary and metastatic tumor growth by antiangiogenesis: involvement of vascular endothelial growth factor. *Nature Medicine* 8: 128-135.

Hardwick, J. S., Kuruvilla, F. G., Tong, J. K., Shamji, A. F., and Schreiber, S. L. (1999) Rapamycin-modulated transcription defines the subset of nutrient-sensitive signaling pathways directly controlled by the Tor proteins. *Proceedings of the National Academy of Sciences of the United States of America* 96: 14866-14870.

Hentges, K. E., Sirry, B., Gingeras, A. C., Sarbassov, D., Sonenberg, N., Sabatini, D., and Peterson, A. S. (2001) FRAP/mTOR is required for proliferation and patterning during embryonic development in the mouse. *Proceedings of the National Academy of Sciences of the United States of America* 98: 13796-13801.

Huang, S. and Houghton. P. J., 2002. Mechanisms of resistance to rapamycins. *Drug Resist. Update,* 4(6), 378-391.

Jain, S., Bicknell, G. R., Whiting, P. H., Nicholson, M. L. (2001). Rapamycin reduces expression of fibrosis-associated genes in an experimental model of renal ischaemia reperfusion injury. *Transplant Proc.* 33(1-2):556-8.

Kahan, B. D., and Camardo, J. S. (2001) Rapamycin: Clinical results and future opportunities. *Transplantation* 72:1181-1193.

Kahan, B. D., Chang, J. Y., and Sehgal, S. N. (1991) Preclinical evaluation of a new potent immunosuppressive agent, rapamycin. *Transplantation* 52: 185-191.

Kirby, B., and Griffiths, C. E. M. (2001) Psoriasis: the future. *British Journal of Dermatology* 144:37-43.

Kirchner, G. I., Winkler, M., Mueller L., Vidal, C., Jacobsen, W., Franzke, A., Wagner, S., Blick, S., Manns M. P., and Sewing K.-F. (2000) Pharmacokinetics of SDZ RAD and cyclosporin including their metabolites in seven kidney graft patients after the first dose of SDZ RAD. British Journal of Clinical Pharmacology 50:449-454.

Kuo, C. J., Chung, J. K., Fiorentino, D. F., Flanagan, W. M., Blenis, J., and Crabtree, G. R. (1992) Rapamycin selectively inhibits interleukin-2 activation of p70 S6 kinase. *Nature* 358: 70-73.

Langmann T, Mauerer R, Zahn A, Moehle C. Probst M. Stremmel W, Schmitz G. (2003) "Real-time reverse transcription-PCR expression profiling of the complete human ATP-binding cassette transporter superfamily in various tissues". *Clin Chem.* 49(2), 230-8.

Lee, J-S, Paull, K., Alvarez, M., Hose, C., Monks, A., Greyer, M., Fojo, A. T., Bates, S. E., 1994. Rhodamine efflux patterns predict P-glycoprotein substrates in the National Cancer Institute drug screen. *Molecular Pharmacology* 46, 627-638.

Li, A. P. (1992) Screening for human ADME/Tox drug properties in drug discovery. *Drug Discovery Today,* 6, 357-366.

Lowden, P. A. S., (1997) Ph.D. Dissertation, University of Cambridge. "Studies on the biosynthesis of rapamycin".

Lyons, W. E., George, E. B., Dawson, T. M., Steiner, J. P., and Snyder, S. H. (1994) Immunosuppressant FK506 promotes neurite outgrowth in cultures of PC12 cells and sensory ganglia. *Proceedings of the National Academy of Sciences of the United States of America* 91:3191-3195.

Main, E. R. G., Fulton, K. F. & Jackson, S. E. (1998). The Context-Dependent Nature of Destabilising Mutations on The Stability of FKBP12. *Biochemistry* 37, 6145-6153.

Main, E. R. G., Fulton, K. F. & Jackson, S. E. (1999a). Folding of FKBP12: Pathway of Folding and Characterisation of the Transition State. *J. Mol. Biol.* 291, 429-444.

McAlpine, J. B., Swanson S. J., Jackson, M., Whittern, D. N. (1991). Revised NMR assignments for rapamycin. *Journal of Antibiotics* 44: 688-690.

Meiering, E. M., Serrano, L. & Fersht, A. R. (1992). Effect of Active Site Residues in Barnase on Activity and Stability. *J. Mol. Biol.* 225, 585-589.

Morice, M. C., Serruys, P. W., Sousa, J. E., Fajadet, J., Ban Hayashi, E., Perin, M., Colombo, A., Schuler, G., Barragan, P., Guagliumi, G., Molnar, F., Falotico, R. (2002). RAVEL Study Group. Randomized Study with the Sirolimus-Coated Bx Velocity Balloon-Expandable Stent in the Treatment of Patients with de Novo Native Coronary Artery Lesions. A randomized comparison of a sirolimus-eluting stent with a standard stent for coronary revascularization. *N. Eng. J. Med.* 346(23):1773-80.

Mothe-Satney, I., Brunn, G. J., McMahon, L. P., Capaldo, C. T., Abraham, R. T., Lawrence, J. C. Jr-. 2000 Mammalian target of rapamycin-dependent phosphorylation of PHAS-I in four (S/T)P sites detected by phospho-specific antibodies. *J Biol Chem.* 275(43), 33836-33843.

Myckatyn, T. M., Ellis, R. A., Grand, A. G., Sen, S. K., Lowe, J. B. 3rd, Hunter, D. A., Mackinnon, S. E. (2002). The effects of rapamycin in murine peripheral nerve isografts and allografts. *Plast. Reconstr. Surg.* 109(7):2405-17.

Navé, B. T., Ouwens, D. M., Withers, D. J., Alessi, D. R., and Sheperd, P. R. (1999) Mammalian target of rapamycin is a direct target for protein kinase B: identification of a convergence point for opposing effects of insulin and amino-acid deficiency on protein translation. *Biochemical Journal* 344:427-431.

NCCLS Reference Method for Broth Dilution Antifungal Susceptibility Testing for Yeasts: Approved Standard M27-A, vol. 17 No. 9. (1997).

Paiva, N. L., Demain, A. L., and Roberts, M. F. (1991) Incorporation of acetate, propionate, and methionine into rapamycin By *Streptomyces hygroscopicus*. *Journal of Natural Products* 54: 167-177.

Paiva, N. L., Demain, A. L., and Roberts, M. F. (1993) The immediate precursor of the nitrogen-containing ring of rapamycin is free pipecolic acid. *Enzyme and Microbial Technology* 15: 581-585.

Perin, E C, (2005), "Choosing a Drug-Eluting Stent: A Comparison Between CYPHER and TAXUS", *Reviews in Cardiovascular Medicine,* 6 (suppl 1), pp S13-S21.

Persidis A. (1999), "Cancer multidrug resistance" Nat. Biotechnol. 17: 94-5

Powell, N., Till, S., Bungre, J., Corrigan, C. (2001). The immunomodulatory drugs cyclosporin A, mycophenolate mofetil, and sirolimus (rapamycin) inhibit allergen-induced proliferation and IL-5 production by PBMCs from atopic asthmatic patients. *J. Allergy Clin. Immunol.* 108(6): 915-7

Rabinovitch, A., Suarez-Pinzon, W. L., Shapiro. A. M. Rajotte, R. V., Power, R. (2002). Combination therapy with sirolimus and interleukin-2 prevents spontaneous and recurrent autoimmune diabetes in NOD mice. Diabetes. 51(3):638-45.

Raught, B., Gingras, A. C., and Sonenberg, N. (2001) The target of rapamycin (TOR) proteins. *Proceedings of the National Academy of Sciences of the United States of America* 98: 7037-7044.

Reather, J. A., (2000), Ph.D. Dissertation, University of Cambridge. "Late steps in the biosynthesis of macrocyclic lactones".

Reitamo, S., Spuls, P., Sassolas, B., Lahfa, M., Claudy, A., Griffiths, C. E.; Sirolimus European Psoriasis Study Group. (2001). Efficacy of sirolimus (rapamycin) administered concomitantly with a subtherapeutic dose of cyclosporin in the treatment of severe psoriasis: a randomized controlled trial. *Br. J. Dermatol.* 145(3):438-45.

Roth T., Burger A. M., Dengler W., Willmann H. and Fiebig H. H. (1999) Human tumor cell lines demonstrating the characteristics of patient tumors as useful models for anticancer drug screening. In: Fiebig H H, Burger A M (eds). Relevance of Tumor Models for Anticancer Drug Development. *Contrib. Oncol.,* 54: 145-156.

Roymans, D., and Slegers, H. (2001) Phosphaditidylinositol 3-kinases in tumor progression. *European Journal of Biochemistry* 268:487-498.

Schwecke, T., Aparicio, J. F., Molnár, I., König, A., Khaw, L. E., Haydock, S. F., Oliynyk, M., Caffrey, P., Cortés, J., Lester, J. B., Böhm, G. A., Staunton, J., and Leadlay, P. F. (1995) The biosynthetic gene cluster for the polyketide immunosuppressant rapamycin. *Proceedings of the National Academy of Sciences of the United States of America* 92: 7839-7843.

Sedrani, R., Cottens, S., Kellen, J., and Schuler, W. (1998) Chemical modifications of rapamycin: the discovery of SDZ RAD. *Transplantation Proceedings* 30: 2192-2194.

Sehgal, S. N., Baker, H., and Vézina, C. (1975) Rapamycin (AY-22,989), a new antifungal antibiotic U. Fermentation, isolation and characterization. *The Journal of Antibiotics* 28: 727-733.

Shepherd, P. R, Withers, D. J., and Siddle K. (1998) Phosphoinositide 3-kinase: the key switch mechanism in insulin signalling. *Biochemical Journal* 333: 471-490.

Smith M. B. and March J. (2001) *March's advanced organic chemistry,* 5th Ed, John Wiley and Sons Inc., UK Steiner, J. P., Hamilton, G. S., Ross, D. T., Valentine, H. L., Guo, H., Connolly, M. A., Liang, S., Ramsey, C., Li, J.-H. J., Huang, W., Howorth, P., Soni, R., Fuller, M., Sauer, H., Nowotnik, A. C., and Suzdak, P. D. (1997) Neutrophic immunophilin ligands stimulate structural and functional recovery in neurodegenerative animal models. *Proceedings of the National Academy of Sciences of the United States of America* 94:2019-2024.

Stein U. Jurchott K. Schlafke M, Hohenberger P. (2002) "Expression of multidrug resistance genes MVP. MDR1, and MRP1 determined sequentially before, during, and after hyperthermic isolated limb perfusion of soft tissue sarcoma and melanoma patients". J Clin Oncol. 20(15): 3282-92.

Szakacs G, Annereau J P, Lababidi S, Shankavaram U. Arciello A, Bussey K J, Reinhold W, Guo Y. Kruh G D, Reimers M. Weinstein J N, Gottesman M M. 2004, "Predicting drug sensitivity and resistance: profiling ABC transporter genes in cancer cells". Cancer Cell. 6(2):129-37.

Tanford, C. (1968). Protein Denaturation. *Adv. Prot. Chem.* 23, 121-282.

Tanford, C. (1970). Protein Denaturation. Part C. Theoretical models for the mechanism of denaturation. *Advances in Protein Chemistry* 24, 1-95

Tang, S. J., Reis, G., Kang, H., Gingras, A.-C., Sonenberg, N., and Schuman, E. M. (2002) A rapamycin-sensitive signaling pathway contributes to long-term synaptic plasticity in the hippocampus. *Proceedings of the National Academy of Sciences of the United States of America* 1:467-472.

Tee, A. R. and Proud. C. G. 2002 Caspase cleavage of initiation factor 4E-binding protein 1 yields a dominant inhibitor of Cap-dependent translation and reveals a novel regulatory motif. *Mol. Cell. Biol.* 22, 1674-1683

Toshima K. and Tatsuta K. (1993) Recent progress in O-glycosylation methods and its application to natural product synthesis. *Chem. Rev.,* 93:1503-1531.

Trepanier D J, Gallant H. Legatt D F, Yatscoff R W. (1998), "Rapamycin: distribution, pharmacokinetics and therapeutic range investigations: an update". *Clin Biochem.* 31(5): 345-51.

Vézina, C., Kudelski, A., and Sehgal, S. N. (1975) Rapamycin (AY-22,989), a new antifungal antibiotic. I. Taxonomy of the producing streptomycete and isolation of the active principle. *The Journal of Antibiotics* 28: 721-726.

Volpe, D. A., Faustino, P. J., Yu, L. X., (2001) Towards standardisation of an in vitro method of drug absorption. *Pharmacopeial Forum,* 27, 2916-2922.

Waller, J. R., and Nicholson, M. L. (2001) Molecular mechanisms of renal allograft fibrosis. *British Journal of Surgery* 88:1429-1441.

Warner, L. M., Adams, L. M., Chang, J. Y., Sehgal, S. N. (1992). A modification of the in vivo mixed lymphocyte reaction and rapamycin's effect in this model. Clin. Immunol. Immunopathol. 64(3):242-7.

Yu, K., Toral-Barza, L. Discafani, C., Zhang, W. G., Skotnicki, J., Frost, P., Gibbons, J. J. (2001) mTOR, a novel target in breast cancer: the effect of CCI-779, an mTOR inhibitor, in preclinical models of breast cancer. Endocrine-Related Cancer 8:249-258.

Zhu, J., Wu J., Frizell, E., Liu, S. L., Bashey, R., Rubin, R., Norton, P., Zern, M. A. (1999). Rapamycin inhibits hepatic stellate cell proliferation in vitro and limits fibrogenesis in an in vivo model of liver fibrosis. *Gastroenterology.* 117 (5):1198-204.

What is claimed is:

1. A method of treatment of cancer or B-cell malignancies which comprises administering to a patient an effective amount of a compound of formula (I):

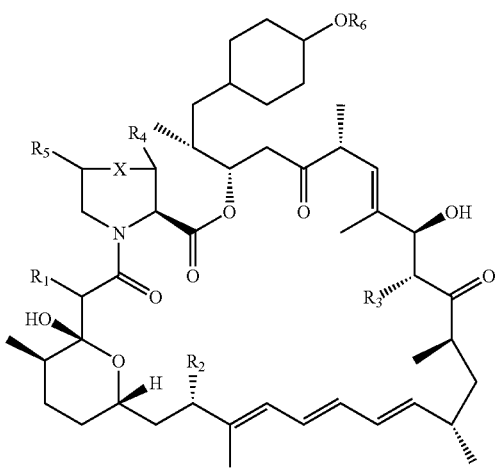

wherein:
X represents bond or $CH_2$;
$R_1$ represents a keto group or (H,H);
$R_2$ represents OH or OMe;
$R_3$ represents H, OH or OMe;
$R_4$ and $R_5$ each independently represent H or OH;
$R_6$ represents —$R_7$, —C(O)$R_7$, —$(CH_2)_2$—O—[$CR_{21}R_{22}$—O]$_a$—C(O)—$R_{23}$, —$CR_{21}R_{22}$—O—C(O)—$R_{23}$, —$POR_{19}R_{20}$, —$PO(OR_{19})(OR_{20})$ or Y—$R_{15}$;
$R_7$ represents —$(CR_8R_9)_m(CR_{10}R_{11})_pCR_{12}R_{13}R_{14}$;
$R_8$ and $R_9$ each independently represent $C_{1-4}$ alkyl, $C_{2-4}$ alkenyl or $C_{2-4}$ alkynyl, any of which groups may optionally be substituted with —$PO(OH)_2$, —$CF_2PO(OH)_2$, —OH, —COOH or —$NH_2$; or $R_8$ and $R_9$ each independently represent H, trifluoromethyl or F;
$R_{10}$, $R_{11}$, $R_{12}$, $R_{13}$ and $R_{14}$ each independently represent $C_{1-4}$ alkyl, $C_{2-4}$ alkenyl or $C_{2-4}$ alkynyl, any of which groups may optionally be substituted with —$PO(OH)_2$, —$CF_2PO(OH)_2$, —OH, —COOH or —$NH_2$; or $R_{10}$, $R_{11}$, $R_{12}$, $R_{13}$ and $R_{14}$ may be independently selected from H, —$(CR_8R_9)_qNH_2$, —$(CR_8R_9)_qOH$, $CF_6$, F, COOH; or $R_{10}$ and $R_{11}$ or $R_{12}$ and $R_{13}$ or $R_{13}$ and $R_{14}$ may be taken together with the carbon to which they are joined to form a $C_{3-6}$ cycloalkyl or a 3- to 6-membered heteroalkyl ring that contains one or more heteroatoms selected from N, O and S and that is optionally, substituted with up to 5 —$(CR_8R_9)_qOH$, —$(CR_8R_9)_qNH_2$ or COOH groups;
Y represents a bond, —C(O)—O—, —$(CH_2)_2$—O—C(O)—O—;
$R_{15}$ represents

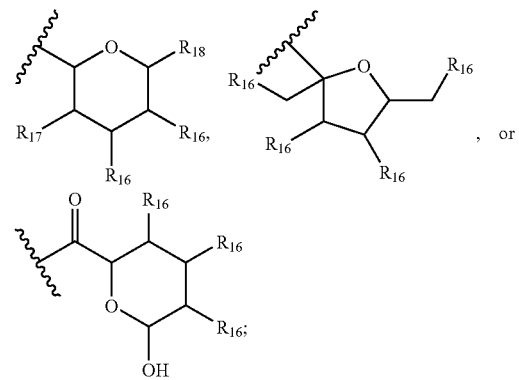

$R_{16}$ are each independently H or OH;
$R_{17}$ is independently selected from H, OH and $NH_2$;
$R_{18}$ is independently selected from H, —$CH_3$, —$CH_2OH$ and —COOH;
provided however that no more than 2 groups selected from $R_{16}$, $R_{17}$ and $R_{18}$ represent H or $CH_3$;
$R_{19}$ and $R_{20}$ each independently represent H or $C_{1-4}$ alkyl or $R_{19}$ and $R_{20}$ together represent =$CH_2$;
$R_{21}$ is independently selected from H, $CH_3$;
$R_{22}$ is independently selected from H, —$CH_3$, —CH=$CH_2$, —$CH_2Cl$, —$CHCl_2$, —$CCl_3$, —CH(OH)Me, —$CH_2OH$, —$CH_2CH_3$, and —CH(Cl)Me;
$R_{23}$ is independently $R_7$, Y—$R_{15}$ or a 5- or 6-membered aryl or heteroaryl ring optionally substituted with between one and three groups selected from OH, F, Cl, Br, $NO_2$ and $NH_2$;
a represents 0 or 1; and m, p and q each independently represent an integer between 0-4;

provided however that the $R_7$ moiety does not contain more than 12 carbon atoms and does contain at least one functional group selected from —PO(OH)$_2$, —CF$_2$PO(OH)$_2$, —COOH, OH or NH$_2$;

or a pharmaceutically acceptable salt thereof;

wherein the cancer is a cancer of the central nervous system, gastric cancer, lung cancer, breast cancer, prostate cancer, ovarian cancer, skin cancer, kidney cancer or uterine cancer.

* * * * *